(12) United States Patent
Wolter

(10) Patent No.: US 7,932,414 B2
(45) Date of Patent: Apr. 26, 2011

(54) SILANE AND SILICIC ACID POLYCONDENSATES WITH RADICALS CONTAINING BRANCHED-CHAIN URETHANE, ACID AMIDE AND/OR CARBOXYLIC ACID ESTER GROUPS

(75) Inventor: Herbert Wolter, Tauberbischofsheim (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 1034 days.

(21) Appl. No.: 10/576,514

(22) PCT Filed: Oct. 25, 2004

(86) PCT No.: PCT/EP2004/012035
§ 371 (c)(1),
(2), (4) Date: Apr. 20, 2006

(87) PCT Pub. No.: WO2005/040249
PCT Pub. Date: May 6, 2005

(65) Prior Publication Data
US 2007/0135572 A1    Jun. 14, 2007

(30) Foreign Application Priority Data
Oct. 24, 2003 (DE) ................... 103 49 766

(51) Int. Cl.
C07F 7/18 (2006.01)
C07F 7/10 (2006.01)

(52) U.S. Cl. ........ 556/438; 556/416; 556/418; 556/419; 556/420; 556/427; 556/430; 556/440; 556/449

(58) Field of Classification Search .................. 556/438, 556/413, 418, 419, 420, 427, 430, 440, 449
See application file for complete search history.

(56) References Cited

U.S. PATENT DOCUMENTS

| | | | |
|---|---|---|---|
| 4,243,692 A | 1/1981 | Scholze et al. | |
| 5,399,738 A | 3/1995 | Wolter et al. | |
| 5,414,093 A | 5/1995 | Wolter | |
| 5,717,125 A | 2/1998 | Wolter et al. | |
| 5,889,132 A | 3/1999 | Rheinberger et al. | |
| 5,919,885 A | 7/1999 | Wolter et al. | |
| 6,124,491 A | 9/2000 | Wolter et al. | |
| 6,222,055 B1 | 4/2001 | Wolter et al. | |
| 6,794,527 B1 | 9/2004 | Wolter et al. | |

FOREIGN PATENT DOCUMENTS

| | | |
|---|---|---|
| DE | 27 58 414 A1 | 12/1977 |
| DE | 40 11 044 A1 | 4/1990 |
| DE | 41 25 201 C1 | 7/1991 |
| DE | 41 33 494 A1 | 10/1991 |
| DE | 44 052 61 A1 | 2/1994 |
| DE | 44 16 857 C1 | 5/1994 |
| DE | 195 25 562 A1 | 7/1995 |
| DE | 196 19 046 A1 | 5/1996 |
| DE | 199 10 895 A1 | 3/1999 |
| EP | 0 450 624 B1 | 4/1991 |
| EP | 0 451 709 B1 | 4/1991 |
| EP | 0 230 342 B1 | 8/1992 |
| EP | 0 682 033 A | 11/1995 |
| EP | 0 837 897 B1 | 7/1996 |
| EP | 0 643 752 B1 | 9/1999 |
| EP | 1 022 012 A | 7/2000 |
| JP | 11-35895 | 2/1999 |
| WO | WO 98/28307 | 7/1998 |

*Primary Examiner* — Elvis O Price
(74) *Attorney, Agent, or Firm* — Stephen A. Bent; Foley & Lardner LLP

(57) ABSTRACT

The invention relates to silane of formula (Ia), wherein the radicals and indices have the following meaning: R is an alkylene, arylene or alkylenearylene group that can be interrupted by one or more oxygen or sulfur atoms or carboxyl or amino groups or can carry said atoms/groups on their ends opposite the silicon atom; $R^1$ is a Z'-substituted alkylene, arylene or alkylenearylene group, which can be interrupted by one or more oxygen or sulfur atoms or carboxyl or amino groups or can carry said atoms/groups on one of their ends; R' is an alkyl, alkenyl, aryl, alkylaryl or arylalkyl group; B and B' can be identical or different, both radicals can have the meaning of a straight-chained or branched organic group with at least one C=C double bond and at least 2 carbon atoms; B' can mean instead thereof but also $-R^2_a Si(OR^3)_{4-a}$ or $-R^2_a R'_b Si(OR^3)_{4-a-b}$, wherein $R^2$ is an alkylene group and R' has the meaning defined above; X represents a group that can enter into a hydrolytic while forming Si—O—Si bridges; Z' means —NH—C(O)O—, —NH—C(O)— or —CO(O)—, wherein the first two radicals are bonded to radical B' by means of the NH group, whereas the carboxylate group can point in both directions except for a minor exception; a represents 1 or 2, and b is 0 or 1. The invention also relates to silicic acid poly (partial) condensates which can be produced by hydrolysis and condensation of said silane, and to the polymer materials with or without filling materials produced therefrom. The invention further relates to a method for the production of the inventive silane.

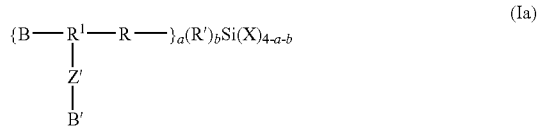

(Ia)

22 Claims, No Drawings

SILANE AND SILICIC ACID POLYCONDENSATES WITH RADICALS CONTAINING BRANCHED-CHAIN URETHANE, ACID AMIDE AND/OR CARBOXYLIC ACID ESTER GROUPS

The present invention relates to novel silanes and silicic acid polycondensates and partial polycondensates formed from them in which there is an organic radical bonded to a silicon atom, said radical being branched and carrying at least one independently organically polymerizable group on each of the two branches or comprising one such a group on one of the two branches and a radical with an additional silicon atom on the other. The second of these two groups, or the silicon atom-containing radical, is bonded via an acid amide, urethane, or carboxylic acid ester group to said organic radical. The invention furthermore comprises various processes for the production of these condensates as well as polymerizates and composites produced therewith.

Silicic acid heteropolycondensates, obtainable by hydrolysis and condensation of silanes with hydrolyzable groups, have been known for a long time (see, for example DE PS 27 58 414). Such condensates can be processed to form many products, for example, to form coverings, coatings, membranes, or bulk materials. The underlying silanes can also comprise double bonds or other organically reactive groups through which they can be polymerized into an organic network (see, for example DE 40 11 044 C2 and DE 44 05 261 A1). A quite specific group of such materials can be obtained from silicic acid polycondensates which comprise a radical bonded to the silicon atom, said radical comprising, in addition to at least one organically reactive group, a free hydroxy or carboxylic acid group. Such silicic acid polycondensates are described in DE 44 16 857 C1. They are suitable, alone, in mixtures, or together with other hydrolyzable, condensable, or polymerizable components, for the production of scratch-resistant coatings, filling materials, adhesive materials, sealing materials, shaped bodies, or embedded materials. The group of compounds described in DE 44 16 857 C1 is furthermore distinguished by the fact that the distance between the silicon atom and reactive or double bond(s) can be set arbitrarily, on account of which the physical characteristics of the condensates or polymerizates thus obtained can be set over wide ranges.

The carboxylic acid group of the carboxylic acid-modified silanes of DE 44 16 857 C1 are charge carriers and thus make possible, for example, the production of dispersions, emulsions, or electropaints. Furthermore, these groups can be complexed with suitable metal compounds of titanium, zirconium, tin, and others, or, in the case of free hydroxy groups, even function as a complexing agents, which can have a positive effect on the X-ray opacity, contact toxicity, and the increase of the index of refraction. The combination of carboxyl groups with polymerizable C=C double bonds in connection with the inorganic silane portion represents an ideal compound for use as polyalkene acids in ionomer cements. However, in many cases one needs systems with a lower hydrophilicity of the matrix than that of the condensates which are obtained from the compounds from DE 44 16 857 C1 since for systems with a lower hydrophilicity of the matrix their water uptake in the presence of moisture would be reduced, their wet strength increased, and the viscosity of the resins lowered. Moreover, a still higher organic cross-linking potential and thus a general increase of the strength is desirable.

It is the objective of the present invention to provide such systems as well as the silanes needed for them and in fact via the insertion of a specific grouping into them which in other respects makes possible a great variability of the other structural elements and thus of the properties of the resins and polymerizates which can be produced.

This objective is realized by the preparation of silanes of the structure (Ia)

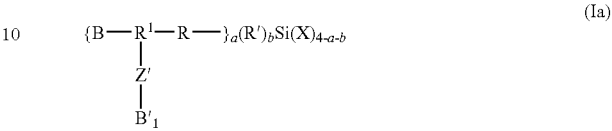

as well as silicic acid polycondensates and silicic acid partial polycondensates comprising the following structural element (Ib):

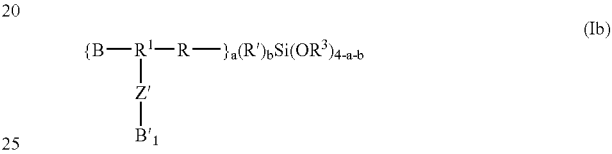

where the radicals and indices have the following meanings:

R is an open-chain and/or cyclic alkylene, arylene, or alkylene-arylene group, with 1 to 10 carbon atoms in each case, which can be interrupted in many cases by one or more oxygen or sulfur atoms or carboxyl or amino groups or can carry such atoms/groups at their end opposite the silicon atom.

$R^1$ is an open-chain and/or cyclic alkylene, arylene, or alkylene-arylene group, with 1 to 10 carbon atoms in each case, which in many cases can be interrupted by one or more oxygen or sulfur atoms or carboxyl or amino groups or can carry such atoms/groups at their ends and which, as can be seen from structures (Ia) and (Ib), carries the group Z' as a substituent;

The radicals $R^3$ bonded to a silicon atom can be the same or different. At least one part thereof must have the meaning of a bond to another silicon atom, in given cases instead of this partially also to another metal atom, which can be inserted into silicic acid heteropolycondensates. In many cases not all the radicals $R^3$ have this meaning. In such cases a part thereof will comprise, instead of this, a hydrogen atom. The silicon atom therefore carries one or more hydroxy groups. If 4-a-b is 3, up to approximately two of the three groups $OR^3$ can be hydroxy, i.e., on average approximately 30% to 70%. If 4-a-b is 2, the number of groups $OR^3$ which are not cross-linked can be on average up to approximately 50%. At 50%, on average one of the two groups is cross-linked with another silicon atom or metal atom. In many of the aforementioned cases a part of the groups $R^3$ can also be, instead of hydrogen, an alkyl group with 1 to 10, preferably 1 to 4, carbon atoms. With regard to the portion of the radicals which represent the bonds to additional Si atoms or other metal atoms, the degree of condensation of the condensate or partial condensate is defined at least to the extent that it can be represented via the structure (Ib) above.

$R^1$ is an open-chain and/or cyclic alkyl, alkenyl, aryl, or alkylaryl, or arylalkyl group, with preferably 1 to 10 carbon atoms. With regard to this let reference be made to the additional explanations of the function of this group, which are found with the definition of the structure (II) described below.

B and B' can be the same or different. Both radicals can have the meaning of a straight-chain or branched organic group with at least one C=C double bond and at least 2, preferably up to 50, carbon atoms. However, instead of this B' can also mean —$R^2_a SiX_{4-a}$ or —$R^2_a R^1_b SiX_{4-a-b}$, where $R^2$ is an alkylene group with 1 to 10 carbon atoms and X is as defined below. The radicals B and also B', if the latter is also a radical with the meaning of a straight-chain or branched organic group with at least one C=C double bond and 2, preferably up to 50, carbon atoms, carry groups which can be polymerized organically in any manner. The at least one C=C double bond in B or B' can, for example, be a component of a vinyl, allyl, norbornene, acryl, and/or methacryl group. In a preferred development each of the groups B and B' carries a Michael system, particularly preferably an acrylate or methacrylate group. In an additional preferred development the radical B carries two or even three Michael systems, for example, acrylate or methacrylate groups. To be named in particular are radicals B and B' which comprise as structural elements $C_2$-$C_4$-alkane diols, the trimethylolpropane group, the pentaerythritol group, or the glycerol structure. B and B' can be acrylic acid ester groups and/or methacrylic acid ester groups of trimethylolpropane, of glycerin, of pentaerythritol, of $C_2$-$C_4$-alkane diols, of polyethylene glycols, of polypropylene glycols, or of, in given cases substituted and/or alkoxylated, bisphenol A or comprise these esters. Also, it is preferred that B, and in given cases B', only comprise one (meth)acrylate group which is bonded via an ester bond of the carboxyl radical to the rest of the molecule. B and B' can have a carbon skeleton. The carbon skeleton(s) (primary and/or secondary chain(s)) can however also be interrupted by heteroatoms or groups such as O, S, SO, NH, NHCO, PR, POR, CONHCO, COO, NHCOO, or the like. The carbon skeleton of B or B' can be exclusively aliphatic and in fact with open and/or closed structures. B and B' can however also have one or more aromatic core(s), condensed systems, triazine groups, or the like, e.g., bisphenol A structures or the like. Furthermore, the groups or structures can be substituted in any manner, e.g., with acid, acid amide, ester, or amino groups.

X is a group which can enter into a hydrolytic condensation reaction with the formation of Si—O—Si bridges. Groups X are designated as inorganic network formers since a silicic acid polycondensate network can form in the hydrolytic condensation reaction. To those skilled in the art it is consequently known what meaning X can assume. Preferably X is a $C_1$-$C_{10}$-alkoxy group, more strongly preferred a $C_1$-$C_4$-alkoxy group, and quite particularly preferred methoxy or ethoxy. X can however also be, if needed, a halide such as Cl, hydrogen, hydroxy, acyloxy with preferably 2 to 5 carbon atoms, alkyl carbonyl with preferably 2 to 6 carbon atoms or alkoxycarbonyl with preferably 2 to 6 carbon atoms. In many cases X can also mean NR" with R" equal to hydrogen, alkyl with preferably 1-4 carbon atoms, or aryl with preferably 6-12 carbon atoms.

Z' has the meaning —NH—C(O)O—, —NH—C(O)—, or —CO(O)—, where the two radicals named first are bonded via the NH group to the radical B' while the carboxylate group can point in both directions, where, when Z' is a —CO(O)— group, its carbon atom is bonded to the radical B', the grouping B'-Z'- may not have the meaning of an acrylate group if B comprises an acrylate group, and the grouping B'-Z' may not be a methacrylate group if B comprises a methacrylate group and preferably moreover with this last-named meaning of Z' and when B' has the meaning of a straight-chain or branched organic group with at least one C=C double bond and at least 2, preferably up to 50, carbon atoms, this C=C double bond must be a part of a (meth)acrylate group as a component of B' at least when B also carries at least one (meth)acrylate group but preferably not only in this special case.

a means 1 or 2, preferably 1, and b can be 0 or 1.

$R^2$ is preferably a radical with 1 to 4 carbon atoms and particularly preferably propylene, and $R^3$ is preferably a radical with 1 to 4 carbon atoms and particularly preferably methyl or ethyl or a bond to another Si atom.

The expressions "(meth)acrylate," "methacrylic acid radical," and the like are intended to be understood in such a manner that optionally a methacrylate or an acrylate or optionally a methacrylic acid radical or an acrylic acid radical is present, or the like.

In a specific development of the silanes according to structure (Ia) B comprises one, two, or three additional groups

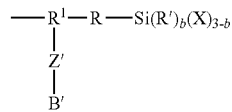

or B' comprises one, two, or three additional groups

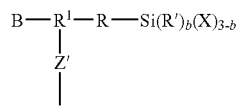

where the radicals and indices have the meaning specified above. In this development there are two or more silane radicals bonded to a radical B or B'.

The hydrolytic condensation of such silanes also leads to silicic acid polycondensates or partial polycondensates of the structure (Ib) which comprise the structural elements above.

According to the invention silanes and silicic acid polycondensates or partial polycondensates derived therefrom are thus provided which are synthesized with the use of structural elements which comprise a partially or completely hydrolyzable/hydrolyzed and/or condensable/condensed silane radical, at least one urethane, acid amide, or carboxylic acid ester group, and either at least two radicals which can be organically polymerized, are arranged so as to be branched, and comprise C=C double bonds, where one of these two radicals is bonded via the stated urethane, acid amide, or carboxylic acid ester group to the silicon atom or one such organically polymerizable radical, and an additional radical comprising a silicon atom and bonded via the said urethane, acid amide, or carboxylic acid ester group to this organic radical. All three molecules can be used according to JTB (ISC) 1992, pages 61-72 and Polymer+Materials Research Symposium 1993, Bayreuth, pages 14-17 for modifications of properties. Therein the additional polymerizable group introduced via the urethane, acid amide, or carboxylic acid ester group enables an additional possibility for cross-linking via the organic radicals compared with the silicic acid polycondensates of DE 44 16 857 C1, whereby stronger polymers can be obtained while the group introduced via this makes possible with an additional silicon atom a densification of the Si—O—Si network in the condensate.

As explained in detail further below, the silanes according to the invention and the silicic acid polycondensates or partial polycondensates derived therefrom can be obtained starting from silanes which comprise a radical B as well as a hydroxy or carboxyl group bonded to a linker between this radical B and the silicon atom. They are described in DE 44 16 857 C1. If one compares the systems which are obtained by direct condensation of such silanes with those of the present invention, it is to be found that the hydrophilicity of the matrix of the systems according to the invention is reduced with respect to those of the systems according to DE 44 16 857 C1 since no, or if a part of the original hydroxy or carboxyl groups is not brought to reaction only a reduced number of, free OH or carboxylic acid groups is/are present so that less viscous resins which have greater wet strength and reduced sensitivity with respect to moisture can be obtained. On the other hand, a high variability can be achieved via the variability of the radicals B, B', R, R$^1$, and R', said variability leading to special and novel combinations of properties. An additional advantage of the present invention lies in the fact that monomer-free condensates, and from them (by polymerization of the groups which can be polymerized organically) organic polymers with good mechanical properties and low shrinkage with viscosity properties, can be obtained which offer good possibilities for processing. Such polymers are designated below as polymerizates if they contain no filling materials and as composites if they contain filling materials.

Preferred are silanes of the structure (Ia) and silicic acid polycondensates with the stated structural elements (Ib), where B has the meaning B"-Z' and Z is an —O—C(O)—, —S—C(O), or —NH—C(O)— group if Z' is —NH—CO— and Z is —O—R$^4$, —S—R$^4$, —NH—R$^4$, —C(O)O—R$^4$, —O—, —S—, —C(O)O— if Z' is —NH—C(O)O—. Therein R$^4$ can have the meaning alkylene, arylene, or alkylarylene with preferably 1 to 10 (for ringless groups) or 6 to 14 (for ring-containing groups) carbon atoms. Therein B," like B, is a straight-chain or branched organic group with at least one C=C double bond and 2 to preferably 50 carbon atoms. B" preferably has the meaning also stated as preferable for B.

The silicic acid polycondensates or partial polycondensates with the structural element of the structure (Ib) can in given cases also be derived from a mixture of various silanes of the structure (Ia) in which the radicals B and/or B' have different meanings. In these condensates the radicals B and/or B' then have no consistent meaning. Since B in these condensates can on the one hand have the meaning as defined for B' but on the other hand also have a meaning differing from it, the structure (Ib) includes silicic acid polycondensates or partial polycondensates in which all the radicals B and B' have the same meaning, silicic acid polycondensates or partial polycondensates in which B and B' have a different meaning but all the radicals B represent the same radical and all the radicals B' represent the same radical, and silicic acid polycondensates or partial polycondensates in which the radicals B' have a meaning different from B and the radicals B and/or the radicals B' are each mixtures of different radicals. Alternatively or in addition, these condensates can comprise foreign metal atoms which can be condensed into such systems, for example, boron, aluminum, germanium, tin, titanium, or zirconium. The metals which are suitable for this are known to those skilled in the art. Silicic acid polycondensates or partial polycondensates are then hetero silicic acid polycondensates or partial polycondensates.

It is to be noted that the components B, B', and Z' do not necessarily have to be present in the silicic acid polycondensates or partial polycondensates according to the invention and with the structural element (Ib) in stoichiometric ratio to one another as follows from the structural element itself. As can also be seen from the description and the examples, the radical B' can, for example, be hypostoichiometric. In these cases the polycondensates or partial polycondensates comprise still free (or alternatively "disguised" or "protected" by re-esterification) hydroxy or carboxyl groups, which, as described above, affects the viscosity behavior of the resin.

Via the organically polymerizable portions of the radicals B and in given cases also B' the silicic acid polycondensates or partial polycondensates according to the invention can be organically cross-linked. In so doing, due to the presence of at least two organically cross-linkable groups per silane molecule, a system is obtained whose organic portion leads to an especially high mechanical strength as well as an improved shrinkage behavior with a reduced shrinkage.

If instead of that, B' is —R$^2_a$SiX$_{4-a}$, or —R$^2_a$R$^1_b$SiX$_{4-a-b}$, the silicon polycondensate according to the invention in this development can form an especially dense Si—O—Si network due to the presence of an additional silicon atom.

The compounds and polycondensates or partial polycondensates according to the invention can be obtained, for example, starting from compounds of the structure II

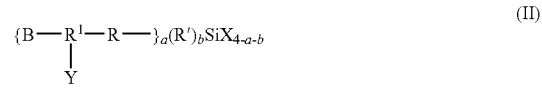

where B, R$^1$, R, R', X, a, and b have the meanings specified for the structures (Ia) and (b) and Y is OH or COOH. The radicals R' and X or substituents located at the silicon atom can be chosen in any manner. In the literature concerning the inorganic-organic materials containing silicon, e.g., those which are commercially available under the name "ORMOCERE"®, much has been written about the respective properties which the respective silane radicals lend to the condensate or organically polymerizable network so that here no detailed explanations are needed. Hydrolyzable radicals are denoted by X. With these groups, which are also designated as inorganic network formers, physical properties of the forming network, such as hardness, flexibility, or the coefficient of thermal expansion, are set in interaction with organic network formers which are present in given cases, here therefore in particular the organically polymerizable groups of the radicals B and in given cases B'. The groups R', which are as a rule not organically polymerizable, are denoted as network modifiers. By choosing them selectively a series of properties can also be affected. Consequently, it is known to those skilled in the art what meaning X can assume. Preferably, X is a C$_1$-C$_{10}$-alkoxy group, more strongly preferably a C$_1$-C$_4$-alkoxy group, and quite particularly preferably methoxy or ethoxy. However, X can, if necessary, also be a halide such as Cl, hydrogen, hydroxy, acyloxy with preferably 2 to 5 carbon atoms, alkyl carbonyl with preferably 2 to 6 carbon atoms, or alkoxycarbonyl with preferably 2 to 6 carbon atoms and in given cases also NR" with R" equal to hydrogen, alkyl with preferably 1-4 carbon atoms, aryl with preferably 6-12 carbon atoms, or another suitable leaving group.

Compounds of the structure (II) are known. Thus, for example, according to DE 44 18 857 C1 compounds of the structure (II) can be produced in which B has the meaning B"-Z—, where B" also has the meaning of a straight-chain or branched organic group with at least one C=C double bond and 2, preferably up to 50, carbon atoms with the preferred developments described for B and Z is an —O—C(O)—, —S—C(O), or —NH—C(O)— group, and in fact by addition reactions of cyclic carboxylic acid anhydride silanes of any ring size with compounds B"(AH), where AH is a hydroxy, a mercapto, or an amino group, where products are obtained in which Y means —COOH. If, instead of this, epoxide silanes are reacted with compounds B"(AH) in which AH is a hydroxy, a mercapto, an amino group, or a carboxylic acid radical, products are obtained in which Y means —OH and Z is —O—R," —S—R," —NH—R," —C(O)—R," —O—, —S—, —NH—, or —C(O)O—. Therein R" has the above-specified meaning. The reaction takes place as a rule without a catalyst in the case of reaction with carboxylic acid anhydride silanes and usually in the presence of a suitable catalyst, e.g., tertiary amines such as triethylamine or phosphines such as triphenylphosphine, and in given cases with increased temperatures if an epoxide silane is used.

In the above-described reactions for the production of the compounds of the structure (II) isomeric and re-esterification products of these compounds can arise depending on the starting materials actually used. This is in particular the case to a significant extent when the radicals X are alkoxy groups, above all methoxy or ethoxy groups. Since in such isomeric and re-esterification products the group Y is partially involved in the isomerization/re-esterification reaction, it is partially no longer free in these products. It has turned out that these byproducts can be drawn upon for the production of the condensates according to the invention just as well as the compounds of the structure (II) themselves, where a separation of the various products is not necessary at all. Instead of this it is sufficient to react the starting materials described for the production of the compounds with the structure (II) with one another in the specified manner and subsequently to subject them to a hydrolysis. In so doing, the group Y is surprisingly free once again while the re-formation of SiOH groups on the contrary drops off sharply and can be essentially suppressed. Thus, as a rule a condensate with an Si—O—Si network is obtained.

The compounds of the structure (II) or their condensation products with group Y released once again are worked up if needed (for example, separated, washed, isolated) and/or, if necessary, dried. In so doing, it should be attended to in particular that no, or as little as possible, H-active impurities are present in the reaction mixture in order to avoid side reactions with the isocyanate in the reaction described below. Then they can be reacted with an isocyanate, where, when Y means OH, a product arises in which Z' is a urethane group —NH—C(O)O— and if Y means COOH, Z' is an acid amide group —C(O)—NH—. Alternatively, they are reacted with a carboxylic acid or an activated carbonyl group (for example, an acid chloride or anhydride) (for Y equal to OH) or an alcohol (for Y equal to COOH) according to current processes, e.g., in the presence of activation agents such as dicyclohexylcarbodiimide, where an ester group —C(O)O— arises which, depending on the starting substance, can point in one or the other direction.

If monomeric compounds of the structure (II) were reacted, silanes of the structure (Ia) are obtained as a rule. They can subsequently be subjected to a hydrolytic condensation in order to arrive at condensates of the structure (Ib).

The production of the compounds according to the invention can be done in different ways. Several process variants are described in principle below.

In the first step of the production in a first development of the invention a compound B"(COOH), where B" has the above meaning, is reacted with a silane comprising an oxirane ring [CH$_2$—CH(O)]—R—Si(X)$_3$, in which R and X have the meanings specified for the structure (Ia), (Ib), and (II). Preferably, X is a methoxy, ethoxy, propoxy, or butoxy group. R can, for example be —CH$_2$—O—(CH$_2$)$_3$. The reaction take place preferably in the presence of a catalyst as explained above and at increased temperatures. As described above, depending on the starting materials and reaction conditions, not only compounds of the structure (II) arise in this reaction but rather also, or even exclusively, condensation products, e.g., by loss of a molecule alcohol with the formation of bridge-type bonds between the oxygen atom of the hydroxy group forming (the group Y in the structure (II)) and a silicon atom according to the following schema, which is shown with the aid of the example of a reaction of methacrylic acid with 3-glycidyloxypropyltrimethoxysilane (GLYMO):

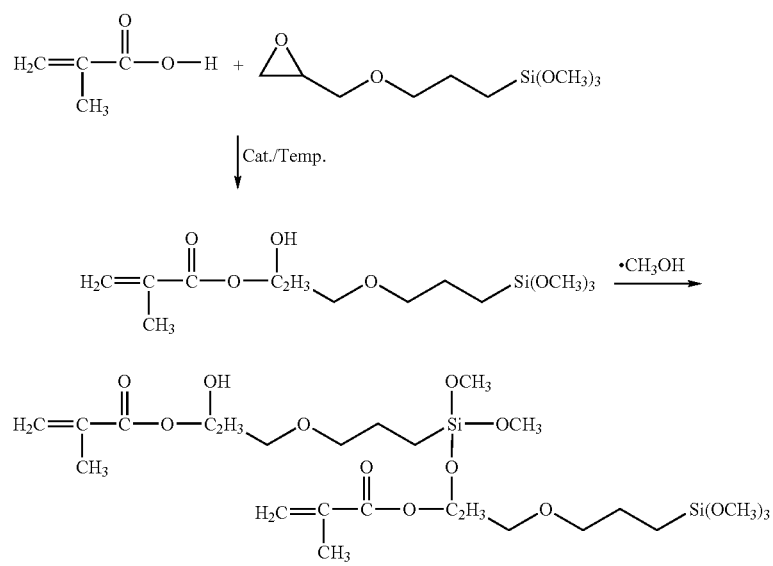

The product or the product mixture can, to the extent that the OH groups are not completely hydrolyzed, be subjected to a hydrolysis which causes, among other things, a condensation of the silane radicals. Surprisingly, in so doing, when an alkoxy group is chosen for X, noteworthy amounts of free hydroxy groups at the silicon atom do not arise without fail, while the hydroxy group at the position Y is re-formed. As already explained above in general, the formation of free hydroxy groups at the silicon atom can be initiated and, if needed, essentially suppressed. Consequently, a silicic acid polycondensate or partial condensate can be obtained which has to a very large, in given cases predominant, extent, or even completely, the following structural elements (III)

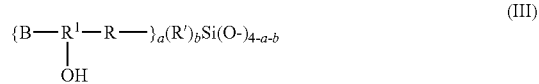

(III)

where the specified radicals and indices have the meaning explained above.

has the meaning above, with a silane $[(CH_2)_n-C_2O_3-CH]-R-Si(X)_3$ comprising a cyclic anhydride radical and in which R and X have the meaning specified for the structures (Ia), (Ib), and (II). Preferably, X is a methoxy, ethoxy, propoxy, or butoxy group. R can, for example, be a propyl group. The reaction can take place without a solvent or catalyst and should preferably take place under an inert atmosphere. It is described in principle and in the example of the reaction of glycerin-1,3-dimethacrylate with triethoxysilyl-propylsuccinic acid anhydride in DE 44 16 857 C1.

In a third development of the invention the first step is carried out by the reaction of a compound B"(OH), where B" has the meaning above, with a silane $[CH_2-CH(O)]-R-Si(X)_3$ comprising an oxiran ring and in which R and X have the meaning specified for the structures (Ia), (Ib), and (II). Preferably, X is a methoxy, ethoxy, propoxy, or butoxy group. R can, for example, be $-CH_2-O-(CH_2)_3$. The reaction takes place preferably in the presence of a catalyst as explained above and at elevated temperatures according to the following schema, which is shown with the aid of the example of a reaction of HEMA (hydroxyethylmethacrylate) with 3-glycidyloxypropyltrimethoxysilane (GLYMO):

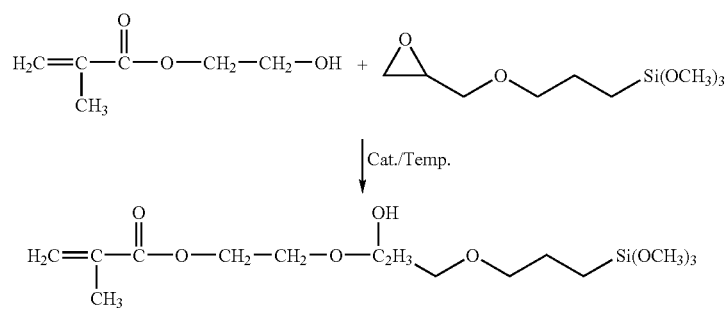

The above-described hydrolysis will however frequently not be necessary since the silylation of the hydroxy group can, in given cases, "protect" it. If some of the OH groups in the reaction mixture are free and some are protected, a condensate of the structure (Ib) can easily be produced therefrom in which the radicals B' are present in excess in relation to B. That this can be desirable is described above.

As described above, also in this reaction, depending on the starting materials, not only compounds of the structure (II) arise in this reaction but rather also, or even exclusively, condensation products, e.g., by loss of a molecule, alcohol with the formation of bridge-type bonds between the oxygen atom of the hydroxy group forming (the group Y in the structure (II)) and a silicon atom. Consequently, the following re-esterifications are possible for this reaction in principle:

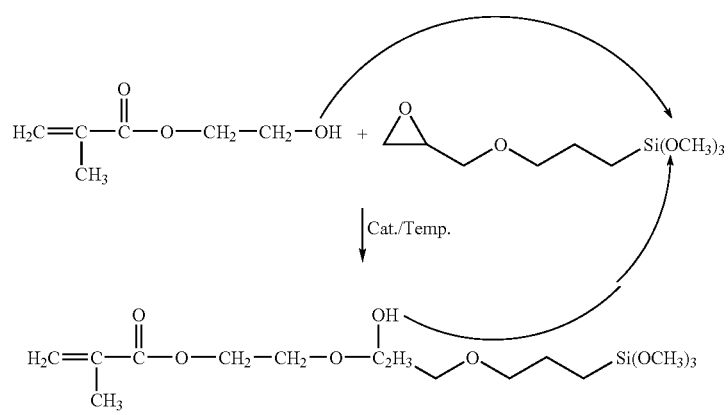

In a second development of the invention the first step is carried out by the reaction of a compound B"OH), where B"

The next step of the production of the condensates according to the invention is done, depending on the product desired, according to the variants described in the following. In a variant (a) the product of the first step is reacted with a compound B'NCO, where B' has the meaning stated above. If Y means OH in the product of the first step, a compound arises with the structure (Ia) or a condensate with the structural element (Ib), where B'-Z' is —B'—NHCOO—. If Y means COOH in the product of the first step, a compound with the structure (Ia) or a condensate with the structural element (Ib) arises, where B'-Z'- means —B'—NH—C(O)—. In a variant (b) the product of the first step, in which Y means COOH, is reacted with a compound B'OH, where B' has the meaning stated above. In so doing, a condensate arises with the structural element (I) in which B'-Z'- means B'—O—C(O)—. In a variant (c) the product of the first step, in which Y means OH, is reacted with a compound B"COOH or a corresponding activated acid derivative, where B' has the meaning stated above. In so doing, a condensate arises with the structural element (I) in which B'-Z'- means B'—C(O)O—. Let it be noted that with the reaction stated last one can also arrive at products which are already known. Thus, one can introduce an additional (meth)acrylic acid radical into this silane, e.g., by reaction of a silane of the structure (II), in which B comprises one or
more acrylate radicals or methacrylate radicals, with an activated (meth)acrylic acid derivative, e.g., the acid chloride. Silanes comprising several methacrylate radicals or several acrylate radicals can however also be obtained in other ways, or are known, on account of which the protection strived for by the present application should not itself extend to the corresponding molecules. It must however be emphasized that the stated reaction by the use, proposed according to the invention, of the reactive OH group (Y) in the molecules with the structure (II) for bonding via an ester group an additional reactive molecular component represents, for one thing, a very comfortable path for producing known and unknown oligo- or poly(meth)acrylate silanes, but, for another thing, is also suitable to make available compounds which previously were not available or had not been synthesized because the reaction path would be too complicated.

The two-step synthesis path of the silanes-proposed according to the invention is illustrated once again below with the aid of several schemata.

1. Carboxy Functionalized Dimethacrylate is from DE 44 16 857

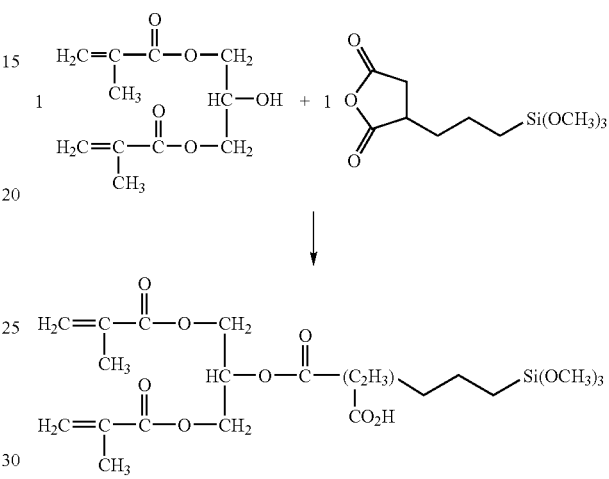

1a. Reaction of Above Carboxy Functionalized Dimethacrylates

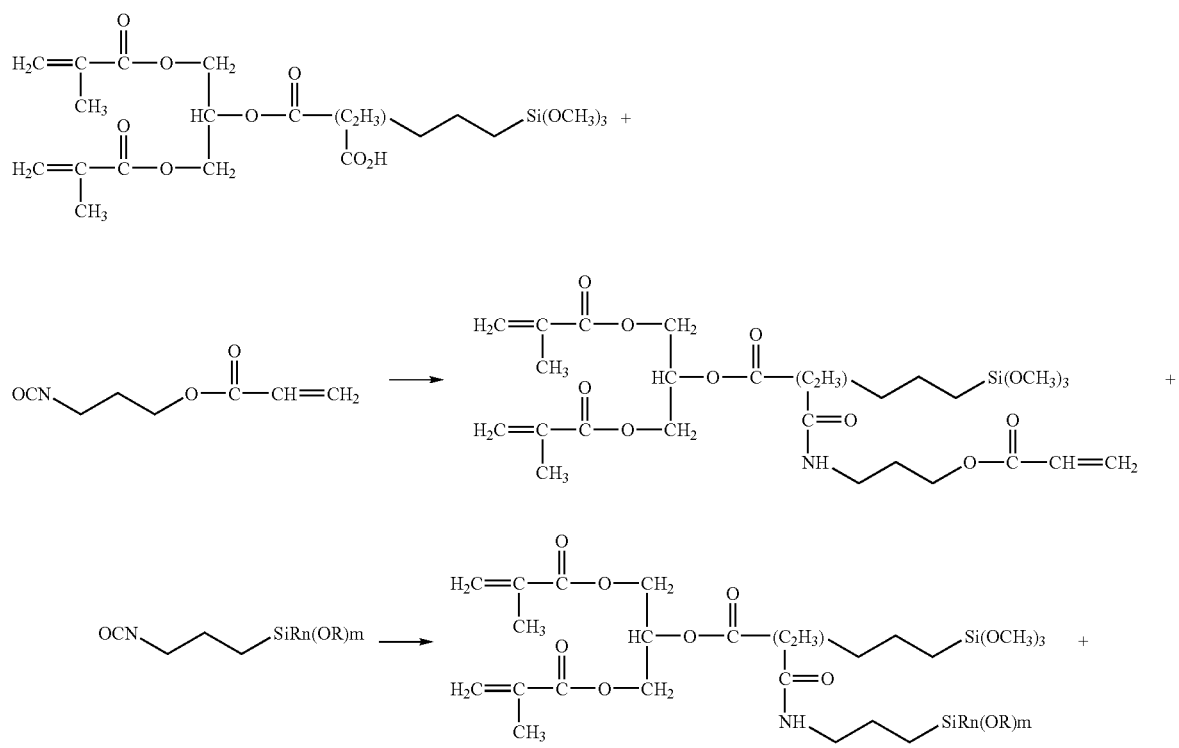

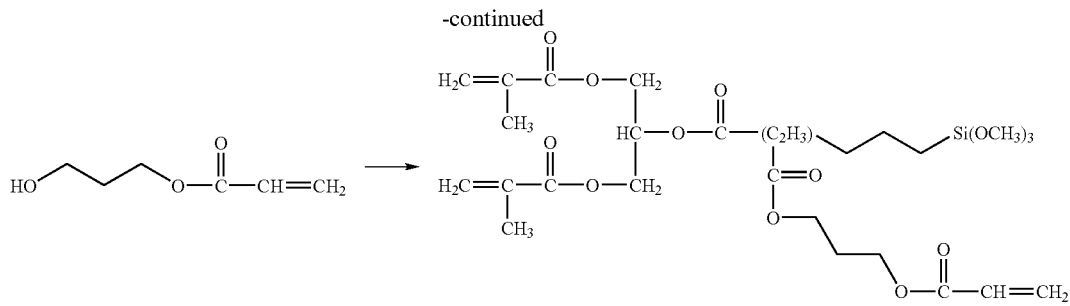
2. Hydroxy Functionalized Dimethacrylate is from DE 44 16 857
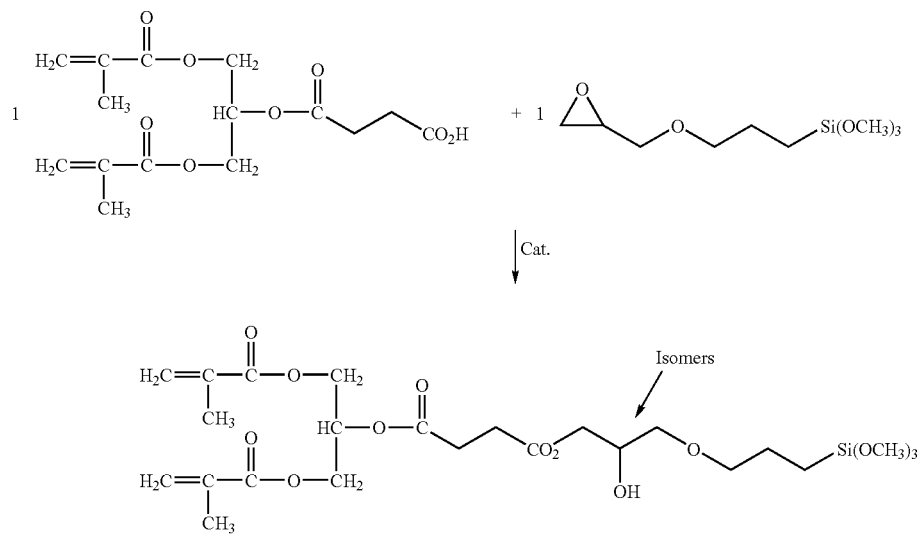
2a. Reaction of Above Hydroxy Functionalized Dimethacrylates
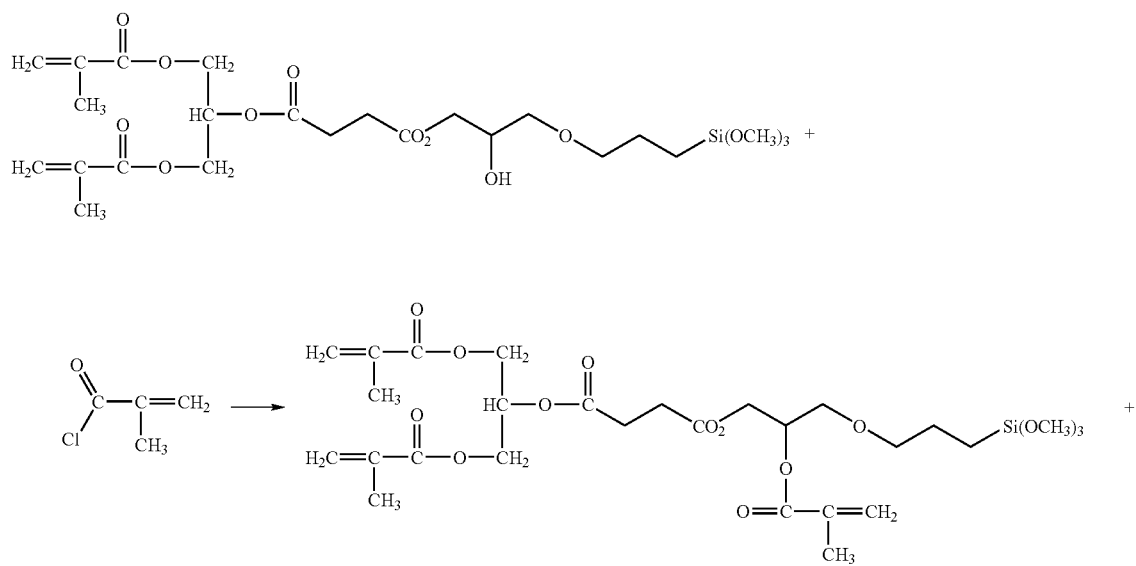

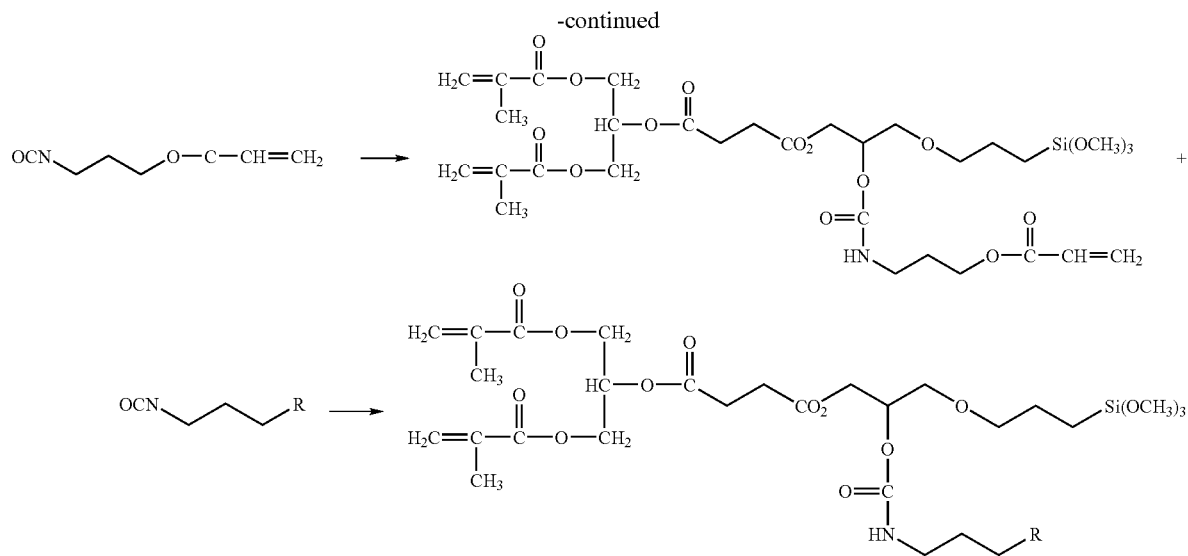
3. Hydroxy Functionalized Dimethacrylate is from DE 44 16 857
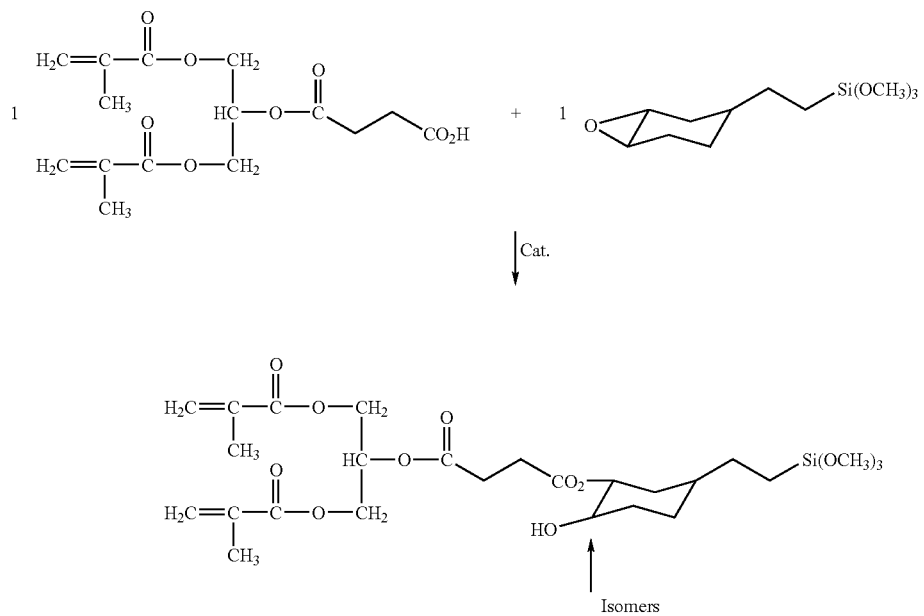
3a. Reaction of Above Hydroxy Functionalized Dimethacrylates
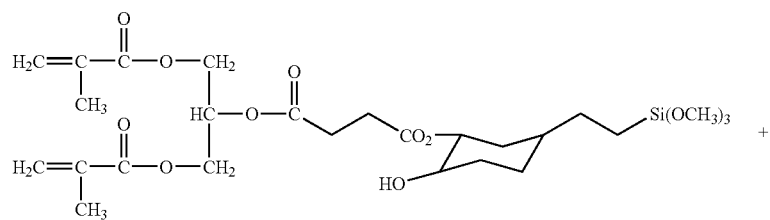

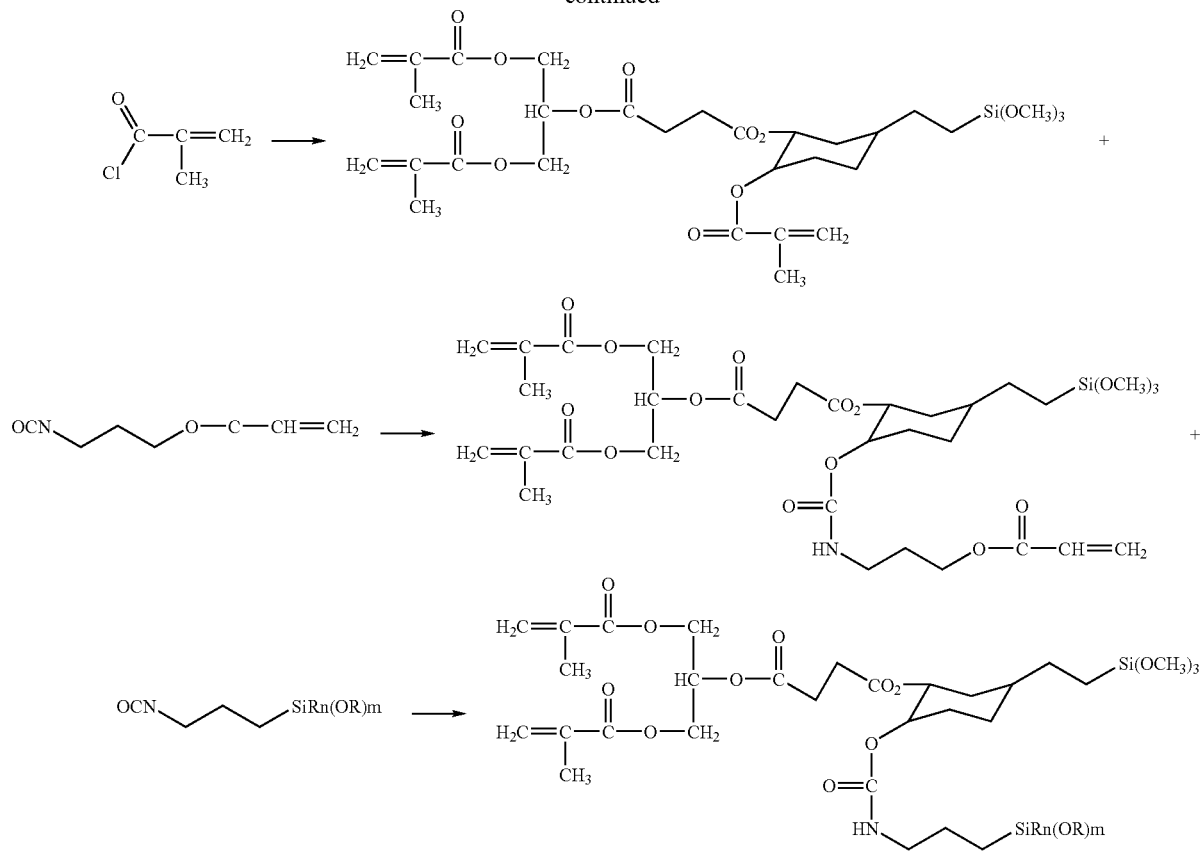
Below the invention is furthermore illustrated with the aid of several chosen reactions:
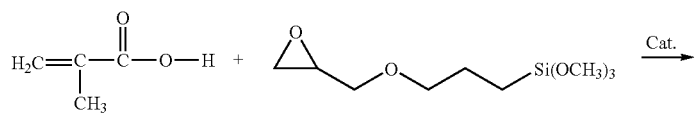
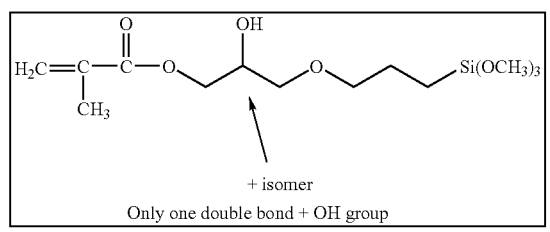
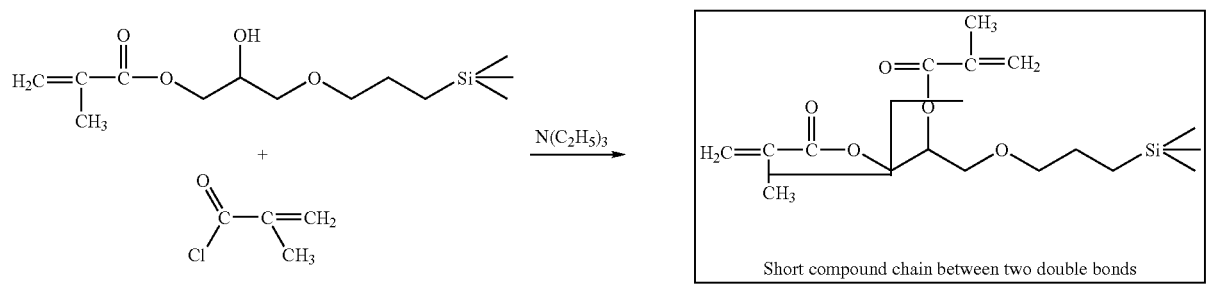

-continued
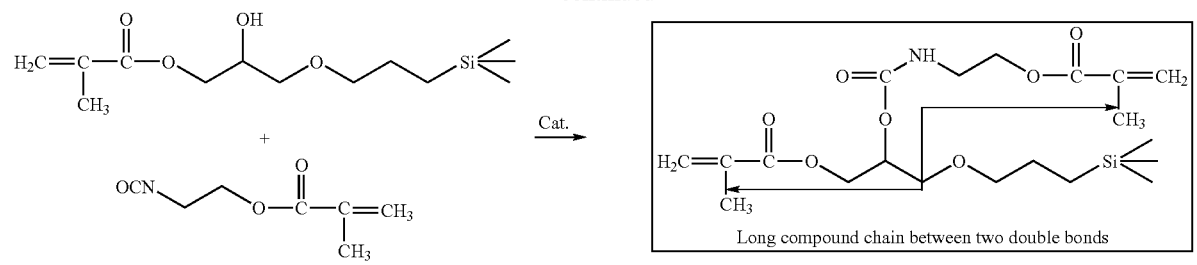
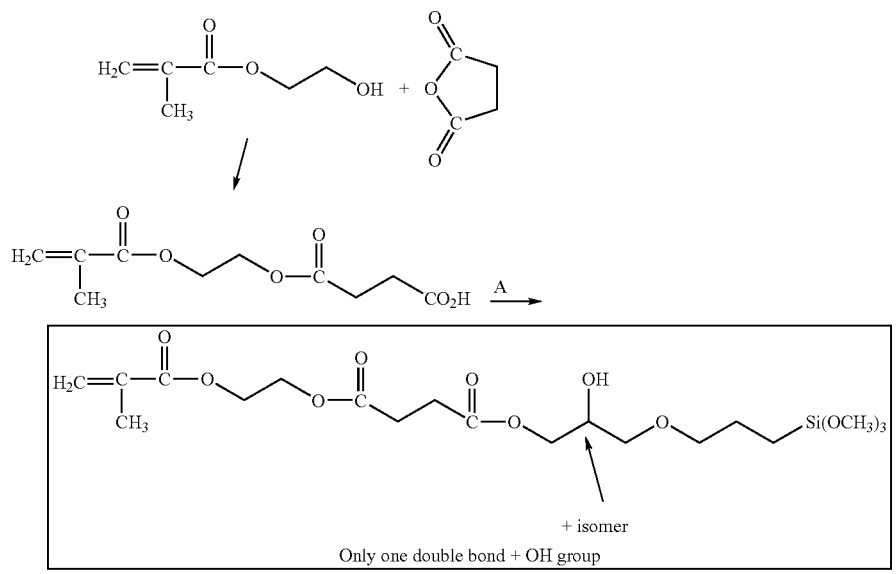
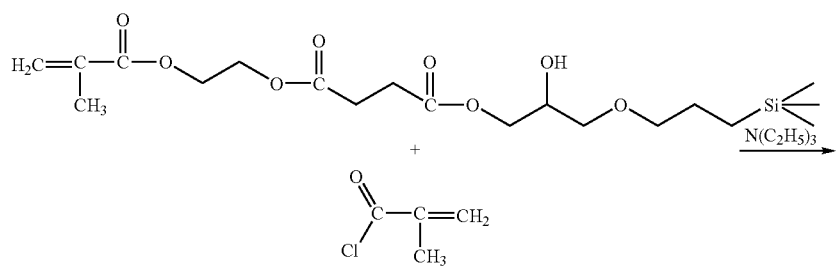
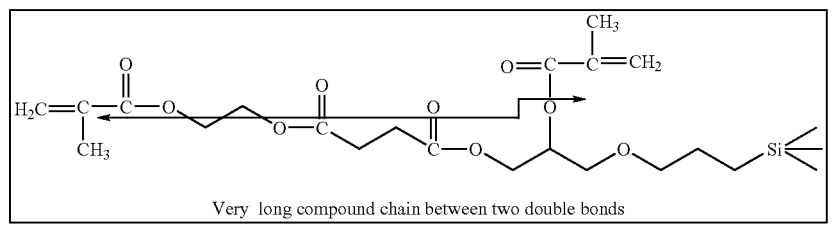
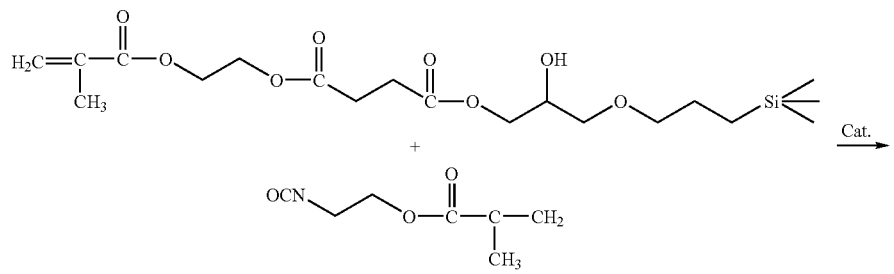

-continued
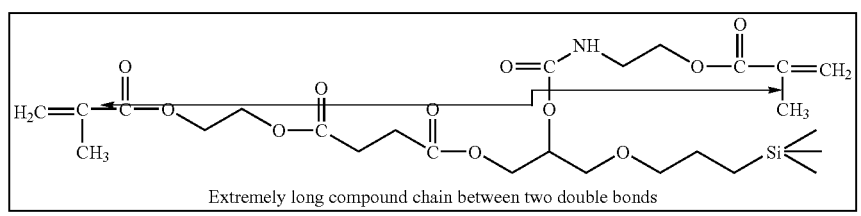
Extremely long compound chain between two double bonds
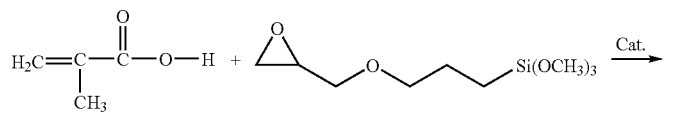
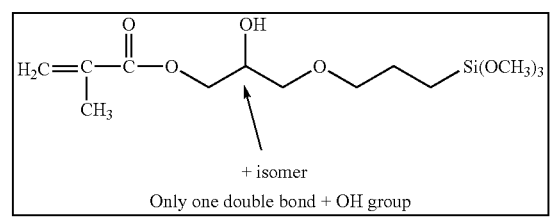
+ isomer
Only one double bond + OH group
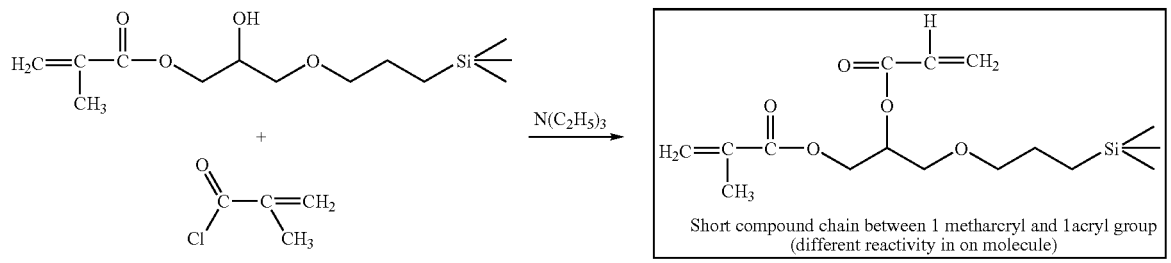
Short compound chain between 1 metharcryl and 1 acryl group
(different reactivity in on molecule)
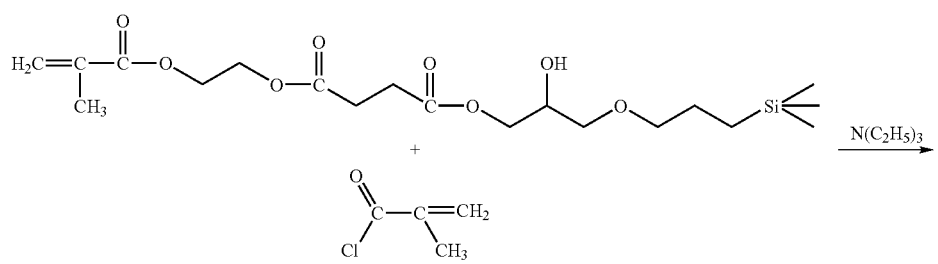
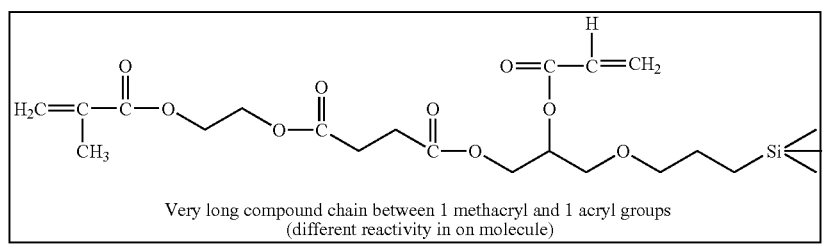
Very long compound chain between 1 methacryl and 1 acryl groups
(different reactivity in on molecule)
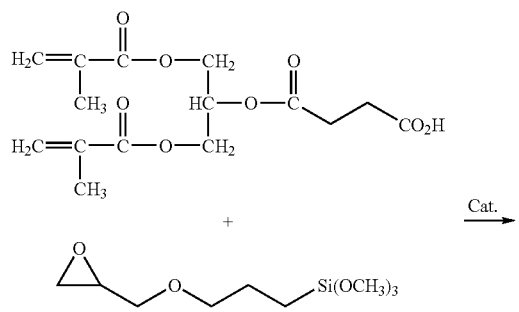

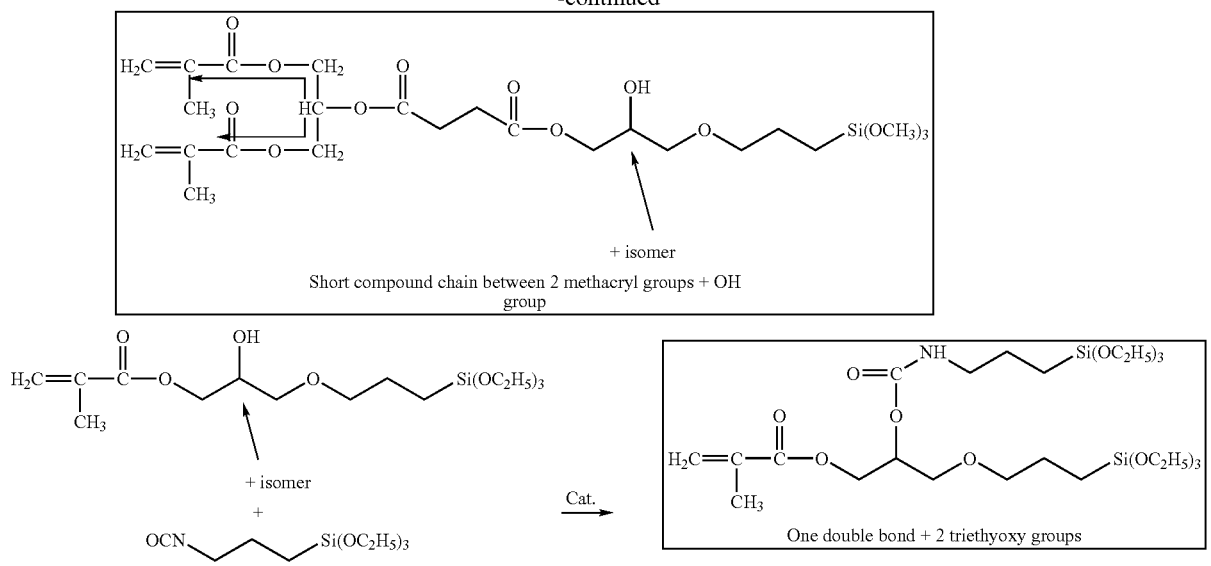

The schemata above show that according to the invention silanes which are highly variable in structure can be produced. Thus, from the product of the reaction of (meth)acrylic acid with GLYMO, which is known from DE 44 16 857 C1, silanes of the structure (Ia) can be produced which depending on the reaction partner used comprise relatively long or relatively short compound chains between the double bonds of the radicals B and B' (see the upper half of the first schema page, where it is pointed out that the reaction paths shown are intended to show as an example the possibilities of the invention but does not have to lead to novel products in all the cases). From the aforementioned German patent the product of the reaction of hydroxyethylmethacrylate (HEMA), succinic acid anhydride, and GLYMO is also known. This product comprises a single methacrylic acid radical as well as a hydroxy group located relatively far removed from it. From this, compounds according to the invention and with two groups comprising double bonds can be produced between which very long or extremely long compound chains are disposed (see lower half of the first schema page, for the products what was stated above applies). The schemata on the upper half of the second page show the possibility of arriving in a relatively simple manner according to the invention at compounds with different radicals B and B', and in fact with variable distances between the radicals B and B' comprising a double bond. Different radicals B and B' in the molecules lend to their organic part a graduated reactivity which, among other things, makes possible a two-step organic polymerization usable, for example, for photostructuring, (1st step: polymerization of the radicals B or B' while retaining a still not completely hardened polymerizate or composite which is accessible to an additional treatment or photostructuring, final cross-linking and hardening by the $2^{nd}$ step of polymerization of the radicals B' or B). In the middle of this page the production of compounds with two groups comprising a double bond located quite near to one another (here methacrylate groups) as well as a third group comprising a double bond disposed further from these (here also a methacrylate group, but it could also be another group comprising a double bond) is shown with aid of an example. The lower part of this page gives an example of how one arrives in a simple way according to the invention at compounds which comprise radicals bonded to different silicon atoms but with identical reactivity. If in this example the ethoxy group of the isocyanate silane or the compound according to structure (II) is exchanged with another hydrolysis-sensitive group with different hydrolysis reactivities, a compound of the structure (I) would be obtained which comprises different leaving groups at two different silicon atoms and thus would be accessible to a graduated hydrolysis and condensation reaction. Such a graduated reactivity is, for example, usable for a simply controlled two-step hydrolysis and condensation reaction, where precautionary measures to be applied otherwise in cases of this type can be omitted. Overall, it is shown in these examples that having two-steps is possible in the area of the inorganic cross-linking and thus the production of resins to be processed and/or in the area of the organic cross-linking and thus in the area of the final processing.

The silanes according to the invention as well as silicic acid polycondensates or partial polycondensates still not completely condensed, alone or in given cases also with additional silanes and/or silicic acid polycondensates or partial polycondensates, can be partially further, or completely, hydrolyzed or condensed. For this, for one thing, silanes and precondensates or partial precondensates thereof which are cocondensable but not copolymerizable, or those which also have polymerizable groups, are suitable. Obviously, the additional components can also be incorporated in an earlier stage if they cannot enter into undesired side reactions with isocyanates or other reactive components. In so doing, there arise condensates with only the structural units, according to the invention, of the structure (Ib) or inorganic networks with Si—O—Si units which comprise these structural units in combination with other units. If B' comprises a silane group already condensed or condensable into a condensate, a particularly dense Si—O—Si structure for that condensate can be obtained.

Instead of this or in addition to it, copolymerizable components can be added to the silanes according to the invention as well as silicic acid polycondensates or partial polycondensates still not completely condensed, where said copolymerizable components, for example, can be radically and/or ionically and/or covalent-nucleophilically polymerized. Radically polymerizable compounds which can be added are, for example, those with C═C double bonds such as, for example, acrylates or methacrylates, where the polymerization is done via the C=C double bonds. Ionically polymerizable compounds which can be added are, for example, ring systems which are polymerizable by cationic opening of the ring such as, for example, spiroorthoesters, spiroorthocarbonates, bicyclic spiroorthoesters, monoepoxides or oligoepoxides or spirosilanes such as, for example, are known from DE 41 25 201 C1. Compounds can however also be used which are ionically as well as radically polymerizable such as, for example, methacryloyl-spiroorthoesters. These are polymerizable radically via the C=C double bond and cationically with ring opening. The production of these systems is described, for example, in the Journal f. prakt. Chemie, Volume 330, Issue 2, 1988, page 316-318. Furthermore, it is, for example, possible to add other known silane-bonded cyclic systems which can be polymerized. Such systems are, for example, those which comprise epoxides. Such systems are described in the production of the spirosilanes in DE 41 25 201 C1. The aforementioned components are polymerized during the polymerization of the resins via their organically polymerizable groups so that a copolymerizate consisting of copolymers and silanes according to the invention can be obtained whose silane groups are present with one another or with additional groups hydrolytically condensed or partially condensed.

The silicic acid polycondensates or partial polycondensates according to the invention, above all when B as well as B' has the meaning of a straight-chain or branched organic group with at least one C=C double bond, and at least 2, and preferably up to 50, carbon atom (where these two radicals naturally do not have to be identical) and if Y is reacted completely or to a high percentage, have a low hydrophilicity of the matrix and consequently take up only a little water in a moist/wet environment. Their wet strength is improved. The radicals B and B' can be inserted, alone or in mixtures and/or cocondensates with additional components such as those mentioned above, into organic polymer structures or they can be cross-linked via these groups as such. Due to the additional organic, cross-linkable group or the additional silyl group which carries B', a example, as, or for the production of, coating, filling, adhesive, casting, and sealing materials, fibers, particles, foils, binding agents for ceramic particles, or as embedded materials from which very scratch-resistant coatings and shaped bodies with high strength can be manufactured. In particular, unfilled polymer materials (polymerizates) as well as (filled) composites can be obtained which were obtained from resins with relatively low viscosity and which have very low shrinkage. Let us also refer to those developments in which the resins, polymerizates, or composites are monomer-free and thus toxicologically/allergically harmless, above all if they have moreover high wet strength (see above).

In a special development of the invention the silicic acid polycondensates or partial polycondensates is mixed before the hardening with one or more additives and/or fillers. Examples of fillers are known from the literature. For example, macrofillers (for example, glass, ceramics, or quartz with particle sizes between 2 to 50 µm) are usable but also other fillers of various materials and with in given cases clearly lower diameters, among these, for example, hybrid fillers or the fine hybrid fillers. Above all with the use of fillers of glass materials such as glass fibers or glass particles, composites are obtained which after organic hardening comprise only minimal shrinkage. Examples for other additives are coloring agents (dyes or pigments), oxidation inhibitors, flow-control agents, UV absorbers, stabilizers, or additives to increase conductivity (for example, graphite powder, silver powder).

The invention will be explained in more detail below with the aid of embodiment examples.

EXAMPLE 1

This example explains the production of a compound of the structure (II) with b equal to 0.

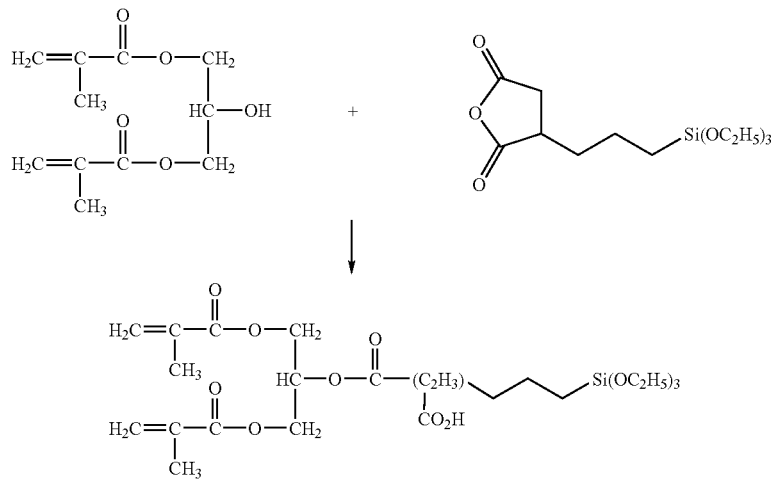

17.0 g (0.05 mol) of triethoxysilylpropylsuccinic acid anhydride are added dropwise under a dry atmosphere to the receiving flask of 12.7 g (0.05 mol) of glycerin-1,3-dimethylacrylate. The reaction can be tracked via the reduction of the anhydride carbonyl bands $$\Box_{as(C=O)}=1786 \text{ cm}^{-1}, \Box_{sy(C=O)}=1864 \text{ cm}^{-1}$$

Since a catalyst or solvent does not have to be added, after the reaction is complete the desired product (liquid) is obtained and can be used without purification for additional reactions.

EXAMPLE 2

This example also explains the production of a compound of the structure (II) with b equal to 0.
Reaction of 3-glycidyloxypropyltrimethoxysilane (GLYMO) with methacrylic acid (MAS)

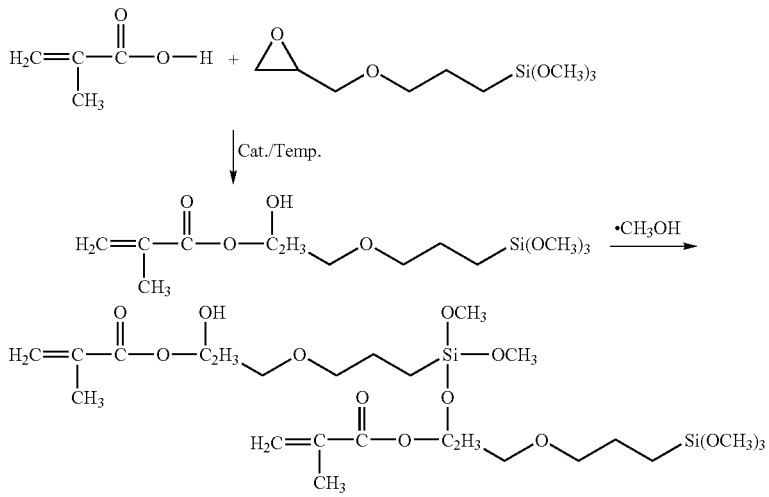

An addition catalyst, BHT as a stabilizer, and subsequently 56.82 g (0.660 mol) of methacrylic acid are added dropwise under a dry atmosphere (oxygen) to the receiving flask of 143.2 g (0.606 mol) of 3-glycidyloxypropyltrimethoxysilane and stirred at ca. 80° (for ca. 24 hours). The reaction can be tracked via the reduction of the carboxylic acid concentration by means of acid titration as well as epoxide conversion by means of Raman spectroscopy/epoxide titration. The bands characteristics for the epoxide group appear in the Raman spectrum at 1256 cm$^{-1}$. The epoxide and carboxylic acid conversion is □99% or □88% (a consequence of the carboxylic acid excess).

EXAMPLE 3

This example shows the production of a compound of the structure (II) or the re-esterification product thereof with b equal to 1.

Reaction of 3-glycidyloxypropylmethyldiethoxysilane with methacrylic acid (MAS)

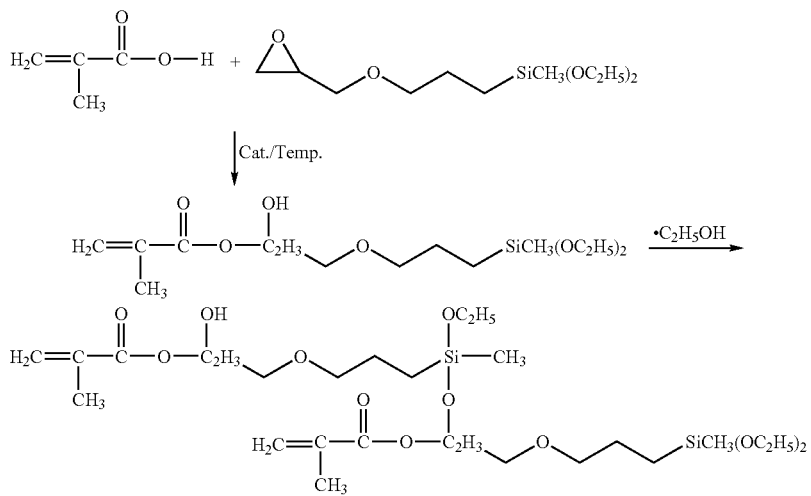

An addition catalyst, BHT as a stabilizer, and subsequently 47.35 g (0.550 mol) of methacrylic acid are added dropwise under a dry atmosphere (oxygen) to the receiving flask of 125.0 g (0.503 mol) of 3-glycidyloxypropylmethyidiethoxysilane and stirred at ca. 80° C. (for ca. 24 hours). The reaction can be tracked via the reduction of the carboxylic acid concentration by means of acid titration as well as epoxide conversion by means of Raman spectroscopy/epoxide titration. The band characteristics for the epoxide group of epoxy silane appears in the Raman spectrum at 1256 cm$^{-1}$. The epoxide and carboxylic acid conversion is □99% or □89% (a consequence of the carboxylic acid excess).

EXAMPLE 4

This example shows the hydrolysis and condensation reaction of the product from example 2.

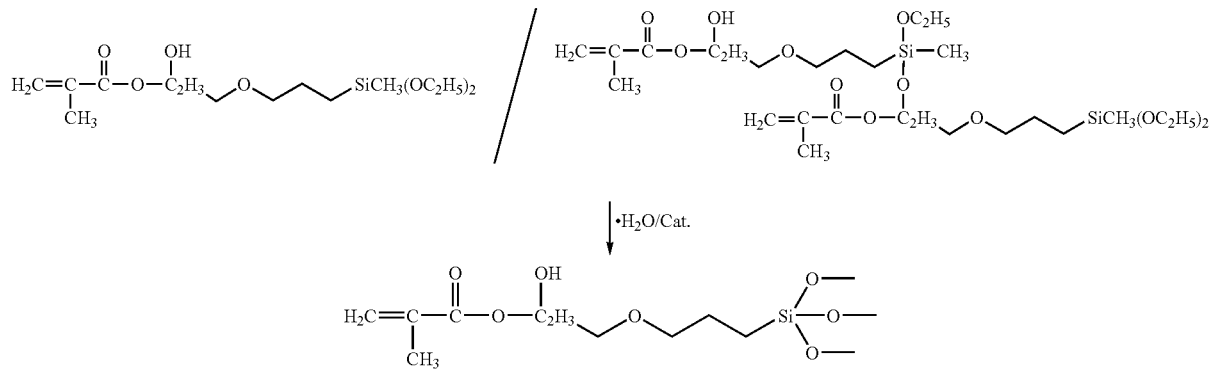

After the addition of ethyl acetate (1000 ml/mol of silane) and H$_2$O for the hydrolysis with NH$_4$F as catalyst the mixture is stirred at room temperature. The course of the hydrolysis is tracked by water titration. After stirring for ca. 2 days at room temperature the work-up is done by repeated shaking with aqueous NaOH, shaking with water, and filtering over a hydrophobized filter. After the addition of BHT and 0.02 mol of 1,6-hexane diol dimethylacrylate, remnants of alcohol and water are removed by first being evaporated in a rotary evaporator at 40° C. and then being drawn off in a oil pump vacuum. A liquid resin results with a viscosity of ca. 15-19 Pa·s at 25° C. (strongly dependent on the precise hydrolysis and workup conditions) and 0.00 mmol of CO$_2$H/g (no more free carboxyl groups).

EXAMPLE 5

The product of example 1 was hydrolyzed and worked up in a comparable manner.

EXAMPLE 6

This example shows the hydrolysis and condensation reaction of the product from example 3.

After the addition of ethyl acetate (1000 ml/mol of silane) and H$_2$O for the hydrolysis with HCl as catalyst the mixture is stirred at 30° C. The course of the hydrolysis is tracked by water titration. After stirring for several days the workup is done by repeated shaking with aqueous NaOH, shaking with water, and filtering over a hydrophobized filter. After this, solvents are evaporated in a rotary evaporator. Then the remaining solvents (alcohol, water, . . . ) are drawn off in a oil pump vacuum. Without the use of reactive diluents (monomers) a liquid resin results with a very high viscosity of ca. 4-6 Pa·s at 25° C. and 0.00 mmol of CO$_2$H/g (no more free carboxyl groups).

EXAMPLE 7

This example shows the addition of an isocyanate in excess to the hydroxy group of the product of example 4.

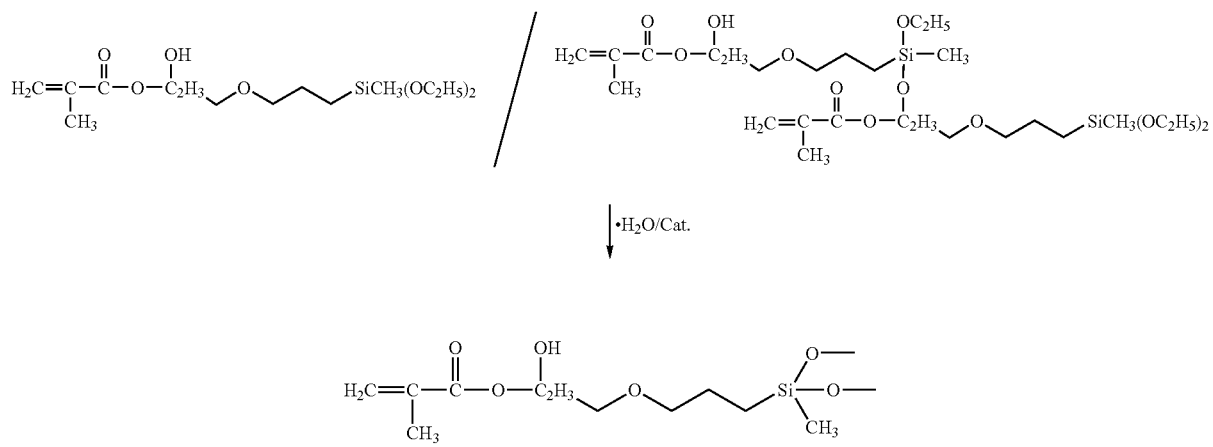

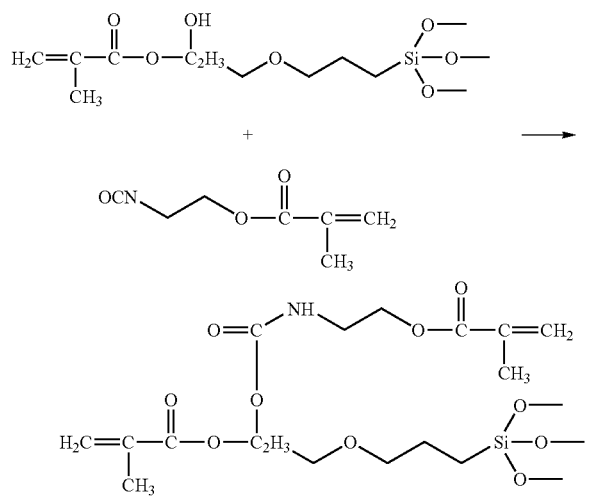

6.52 g (excess: 0.042 mol) of methacrylic acid isocyanatoethylester are added dropwise under a dry atmosphere (oxygen) at room temperature with stirring to the receiving flask of 18.6 g (0.06 mol) of the above resin, and stirred at room temperature (for ca. 3 hours). The reaction can be tracked via the reduction of the OCN band by means of the IR spectrum. The band characteristic of the OCN group appears in the IR spectrum at 2272 cm$^{-1}$. After 1 hour in an oil pump vacuum a viscous resin results.

IR data: $\square_{(OH\square\,educt)}$~3500 cm$^{-1}$, (unreacted OH since reaction was only with 0.7 moles of methacrylic acid isocyanatoethylester)

$\square_{(NH\square\,urethane)}$~3370 cm$^{-1}$
$\square_{(C=O\square\,methacylate/urethane)}$~1721 cm$^{-1}$
$\square_{(C=C\square\,methacylate)}$~1638 cm$^{-1}$

EXAMPLE 8

This example shows the addition of an isocyanate to the product of example 5.

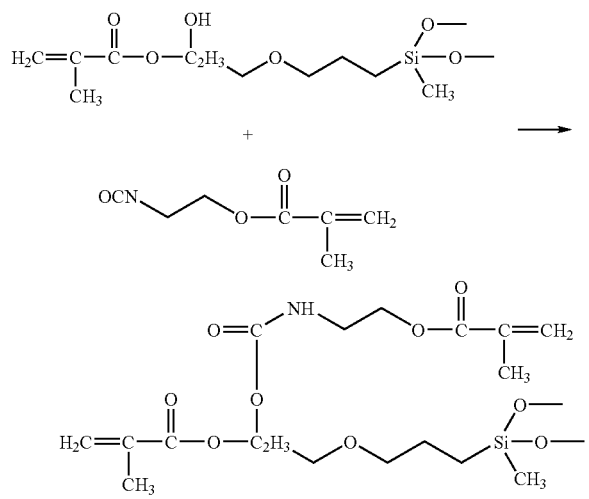

8.69 g (0.056 mol) of methacrylic acid isocyanatoethylester are added dropwise under a dry atmosphere (oxygen) at room temperature with stirring to the receiving flask of 21.2 g (0.08 mol) of the above resin and stirred at 30° C. The reaction can be tracked via the reduction of the OCN band by means of the IR spectrum. The band characteristic of the OCN group appears in the IR spectrum at 2272 cm$^{-1}$. A liquid resin results with a viscosity of ca. 18-20 Pa·s at 25° C. (strongly dependent on the precise synthesis and workup conditions, in particular also the precursors).

IR data: $\square_{(OH\square\,educt)}$~3500 cm$^{-1}$, (unreacted OH since reaction was only with 0.7 moles of methacrylic acid isocyanatoethylester)

$\square_{(NH\square\,urethane)}$~3373 cm$^{-1}$
$\square_{(C=O\square\,methacylate/urethane)}$~1721 cm$^{-1}$
$\square_{(C=C\square\,methacylate)}$~1638 cm$^{-1}$

EXAMPLE 9

This example describes the polymerization of the organically polymerizable groups of the condensate from example 7.

Resin from example 7 with 1% Lucirin TPO is shaped as a rod (2×2×25 mm$^3$). The methacrylate groups are reacted in the framework of a photoinduced radical polymerization, in which the resin hardens. By means of a 3-point bending experiment the modulus of elasticity as well as the fracture strength of the resulting rods is determined after 1.5 days under air or water at 40° C.

Modulus of elasticity=2.80 GPa(air)/2.50 GPa(water)

Fracture strength=109 MPa(air)/89 MPa(water)

By means of the buoyancy method the following shrinkage values are obtained in the framework of a photoinduced radical polymerization:

4.3% by volume/5.3% by volume after storage of 15 minutes for 1 day

Thus, outstanding data result, on account of which the product can be used, for example, as a matrix system for composites usable for various purposes.

COMPARATIVE EXAMPLE 1

Resin from example 4 with 1% Lucirin TPO is shaped as a rod (2×2×25 mm$^3$). The methacrylate groups are reacted in the framework of a photoinduced radical polymerization, in which the resin hardens. By means of a 3-point bending experiment the modulus of elasticity as well as the fracture strength of the resulting rods is determined after 1.5 days under air or water at 40° C.

Modulus of elasticity=2.21 GPa(air)/1.64 GPa(water)

Fracture strength=89 MPa(air)/55 MPa(water)

By means of the buoyancy method the following shrinkage values are obtained in the framework of a photoinduced radical polymerization:

5.3% by volume/6.4% by volume after storage of 15 minutes for 1 day

According to the invention clearly lower mechanical characteristic data (caused by the presence of only one double bond per silane unit), a clearly stronger drop-off due to water storage, and surprisingly a shrinkage higher by ca. 1% by volume than on the basis of the resin system of example 6.

EXAMPLE 10

This example shows the production of a composite on the basis of the resin system of example 6.

1% Lucirin TPO is dissolved in the resin from example 6 and a mixture of fillers (77% by weight) consisting of a fine glass (silanized) from the Schott company (on average ca. 3 μm diameter) and Aerosil 8200 (partially silanized) (from the Degussa company) is incorporated. The resulting well-processible composite is shaped as a rod (2×2×25 mm³) and hardened in the framework of photoinduced radical polymerization. By means of a 3-point bending experiment the modulus of elasticity as well as the fracture strength of the resulting rods is determined after 1.5 days under air or water at 40° C.

Modulus of elasticity=13.3 GPa(air)/12.4 GPa(water)

Fracture strength=145 MPa(air)/135 MPa(water)(individual values in each case still clearly higher)

In the framework of photoinduced radical polymerization the following shrinkage values were determined:

By means of the buoyancy method □ 2.1% by volume/2.4% by volume after storage of 15 minutes for 1 day Thus, outstanding data result even with a non-optimized standard filler mixture with comparatively still low filler content.

EXAMPLE 11

This example describes the polymerization of the organically polymerizable groups of the condensate from example 8.

Resin from example 8 with 1% Lucirin TPO is shaped as a rod (2×2×25 mm³). The methacrylate groups are reacted in the framework of a photoinduced radical polymerization, in which the resin hardens. By means of a 3-point bending experiment the modulus of elasticity as well as the fracture strength of the resulting rods is determined after 1.5 days under air or water at 40° C.

Modulus of elasticity=2.30 GPa(air)/2.10 GPa(water)

Fracture strength=104 MPa(air)/82 MPa(water)

By means of the buoyancy method the following shrinkage values are obtained in the framework of a photoinduced radical polymerization:

4.3% by volume/5.1% by volume after storage of 15 minutes for 1 day

Thus, outstanding data result, on account of which the product can be used, for example, as a monomer-free matrix system for composites:

COMPARATIVE EXAMPLE 2

The condensate from example 5 with 1% Lucirin TPO is shaped as a rod (2×2×25 mm³). The methacrylate group are reacted in the framework of a photoinduced radical polymerization, in which the resin hardens. By means of a 3-point bending experiment the modulus of elasticity as well as the fracture strength of the resulting rods is determined after 1.5 days under air or water at 40° C.

Modulus of elasticity=1.74 GPa(air)/1.13 GPa(water)

Fracture strength=70 MPa(air)/50 MPa(water)

By means of the buoyancy method the following shrinkage values are obtained in the framework of a photoinduced radical polymerization:

5.4% by volume/6.0% by volume after storage of 15 minutes for 1 day

Clearly lower mechanical characteristic data result, a clearly stronger drop-off due to water storage, and surprisingly shrinkage higher by ca. 1% by volume than on the basis of the resin system of example 11.

EXAMPLE 12

This is an example which shows an isocyanate addition to a silane of the structure (II) in the ratio 1:0.2 and thus the prerequisites for the production of a silicic acid polycondensates or partial polycondensate which still has free hydroxy groups.

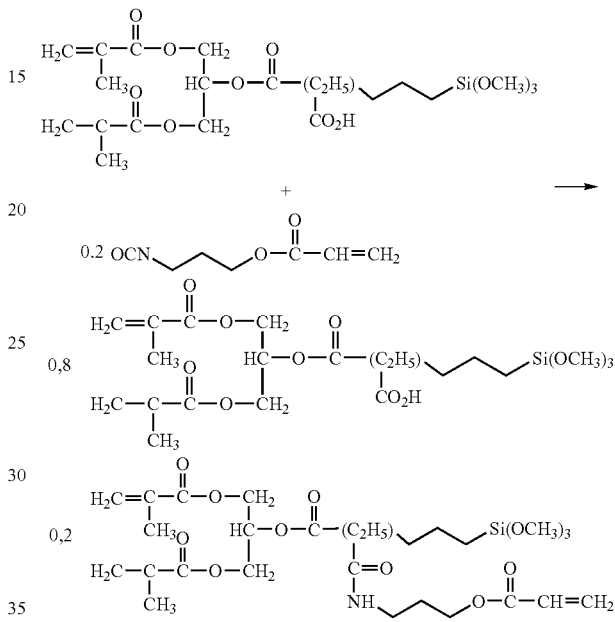

3.10 g (0.02 mol) of methacrylic acid isocyanatoethylester are added dropwise under a dry atmosphere (oxygen) at 40° C. with stirring to the receiving flask of 0.10 mol of the compound from example 1 and diazabicyclooctane as catalyst and stirred at 40° C. The reaction can be tracked via the reduction of the OCN band by means of the IR spectrum. The band characteristic of the OCN group appears in the IR spectrum at 2272 cm⁻¹. The successfully synthesis can be demonstrated with the aid of $^1$H, $^{13}$C, and FT-IR spectroscopy. The resulting liquid product consisting of educt with 2 double bonds and reaction products with 3 double bonds can be isolated by a customary workup or preferably, directly after customary processes, subjected to further reaction, that is, hydrolysis/condensation of the Si(OCH₃)₃ groups.

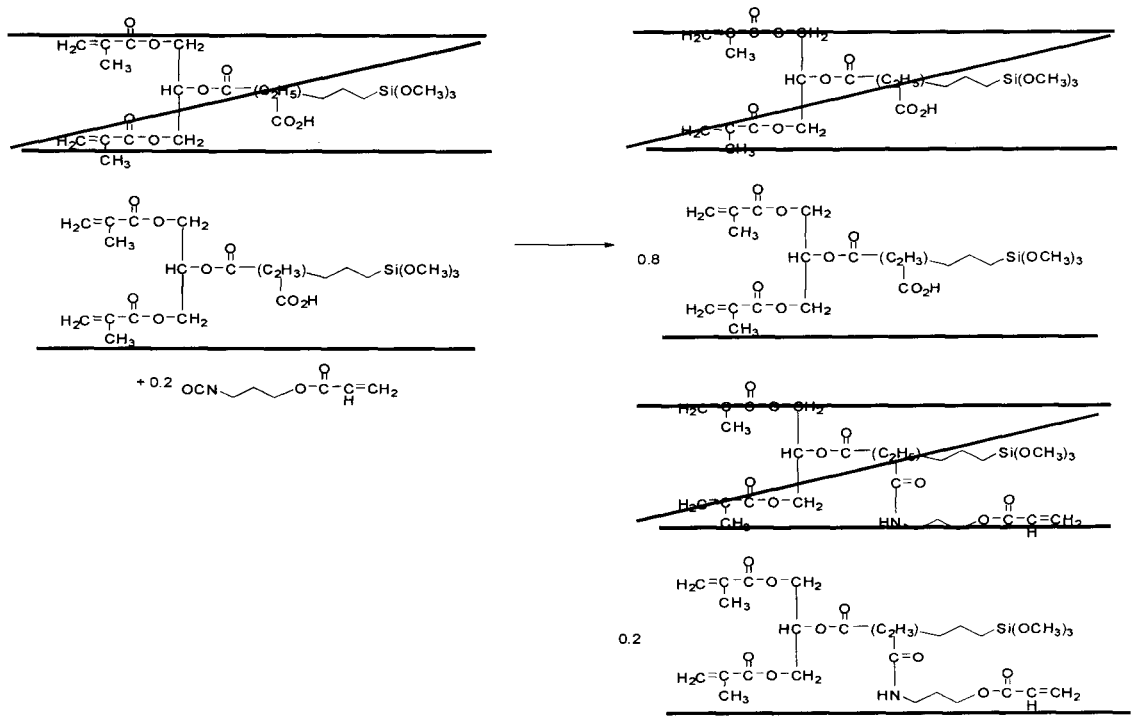

The invention claimed is:
1. Silane of the structure (Ia) below

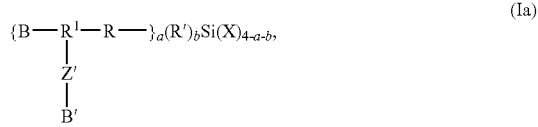

where the radicals and indices have the following meanings:
R is an open-chain and/or cyclic alkylene, arylene, or alkylene-arylene group, with 1 to 10 carbon atoms in each case, which can be interrupted by one or more oxygen or sulfur atoms or carboxyl or amino groups or can carry such atoms/groups at their end opposite the silicon atom, $R^1$ is a Z'-substituted, open-chain and/or cyclic alkylene, arylene, or alkylene-arylene group, with 1 to 10 carbon atoms in each case, which can be interrupted by one or more oxygen or sulfur atoms or carboxyl or amino groups or can carry such atoms/groups at their end opposite the silicon atom, R' is an open-chain and/or cyclic alkyl, alkenyl, aryl, or alkylaryl, or arylalkyl group, with preferably 1 to 20 carbon atoms, B and B' can be the same or different, both radicals can be a straight-chain or branched organically polymerizable group with at least one C=C double bond and at least 2 carbon atoms, instead of this B' can also be —$R^2_a$Si$X_{4-a}$ or —$R^2_a R^1_b$Si$X_{4-a-b}$, where $R^2$ is an alkylene group with 1 to 10 carbon atoms and R' is defined as above, X is a group which can enter into a hydrolytic condensation reaction with the formation of Si—O—Si bridges, Z' is selected from —NH—C(O)O—, —NH—C(O)—, or —CO(O)—, where the two radicals named first are bonded via the NH group to the group B' while the carboxylate group can point in both directions, where, when Z' is a —CO(O)— group, the carbon atom of which is bonded to the radical B', and B' is a straight chained or branched organically polymerizable group having at least one C=C double bond and at least 2 carbon atoms, this C=C double bond must be part of a (meth)-acrylate residue as component of B', and the grouping B'-Z'- is not an acrylate group if B comprises an acrylate group, and the grouping B'-Z'- is not a methacrylate group if B comprises a methacrylate group, a is 1 or 2, and
b is 0 or 1.

2. Silane according to claim 1, in which
$R^1$ is a group with 1 to 10 carbon atoms and/or
B and optionally also B' carries at least one Michael system, and/or
X is a $C_1$-$C_{10}$ alkoxy group.

3. Silane according to claim 1, in which
the radicals B and optionally also B' are acrylic acid ester groups and/or methacrylic acid ester groups of trimethylolpropane, of glycerin, of pentaerythritol, of $C_2$-$C_4$-alkane diols, of polyethylene glycols, of polypropylene glycols, or in given cases substituted and/or alkoxylated, bisphenol A or comprise these esters.

4. Silane according to claim 1, in which
the radicals B and optionally also B' comprise an end-to-end carbon skeleton or this skeleton is interrupted by heteroatoms or groups chosen from among O, S, SO, NH, NHCO, PR, POR, CONHCO, COO, NHCOO.

5. Silane according to claim 1, in which a is equal to 1 and b is equal to 0.

6. Silane according to claim 1, in which a is equal to 1 and b is equal to 1.

7. Silane according to claim 1, in which B is a (meth)acrylate group or comprises a radical which is bonded via a (meth)acrylate group to $R^1$ and comprises no additional or one, two, or three (meth)acrylate groups.

8. Silane according to claim 1, in which B is bonded via a group Z to $R^1$, where Z is an —O—C(O)—, —S—C(O), or —NH—C(O)— group if Z' is —NH—CO— and Z is —O—$R^4$, —S—$R^4$, —NH—$R^4$, —C(O)O—$R^4$, —O—, —S—, —NH—, or —C(O)O— if Z' is —NH—C(O)O—, where $R^4$ is selected from alkylene, arylene, or alkylarylene with 1 to 10 (for ringless groups) or 6 to 14 (for ring-containing groups) carbon atoms.

9. Silane according to claim 7, in which Z' is —NH—C(O)O— or —NH—C(O).

10. Silane according to claim 7, in which b is zero.

11. Silane according to claim 7, in which b is 1 and R' is a $C_1$-$C_4$ alkyl group.

12. Silane according to claim 1, in which B' is a (meth)acrylate group or comprises a radical which is bonded via a (meth)acrylate group to $R^1$ and comprises no additional or one, two, or three (meth)acrylate groups.

13. Silane according to claim 1, in which B' is a dialkoxyalkylsilylalkylene group with 1 to 4 carbon atoms in the alkyl and alkoxy groups and 1 to 8 carbon atoms in the alkylene group.

14. Silane according to claim 1, in which B comprises at least one additional group

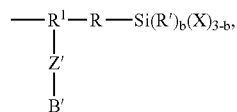

or B' comprises at least one additional group

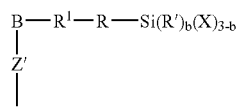

where the radicals and indices have the meanings specified in claim 1 for the structure (1a).

15. Process for the production of a silane with the structure (Ia) as defined in claim 1, comprising the following steps
(a) preparation of a compound with the structure (II) or an isomer
a re-esterification product, or one of this compound's condensation products arising by loss of an alcohol molecule

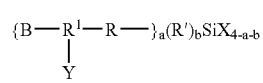

(II)

in which B, $R^1$, R, R', X, a, and b have the meanings specified in claim 1 for the structure (Ia) and Y is OH or COOH,
and Y means COOH,
(b) reaction of this compound or of the isomer, re-esterification product,
or condensation product with a compound
B'NCO,
in which B' has the meaning specified in claim 1 for structure (Ia), and
(c) in given cases, workup of the product.

16. Process for the production of a silane with the formula (Ia) as defined in claim 1, including the following steps:
(a) preparation of a compound with the structure (II) or an isomer
a re-esterification product, or one of this compound's condensation products arising by loss of an alcohol molecule

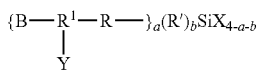  (II)

in which B, $R^1$, R, R', X, a, and b have the meanings specified in claim 1 for the structure (Ia),
and Y means COOH,
(b) reaction of this compound or of the isomer, re-esterification product,
or condensation product with a compound
B' OH,
in which B' has the meaning specified in claim 1 for structure (Ia), and
(c) in given cases, workup of the product.

17. Process for the production of a silane with the formula (Ia) as defined in claim 1,

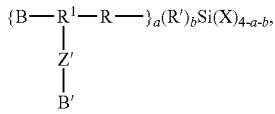  (Ia)

where the radicals and indices have the following meanings:

R is an open-chain and/or cyclic alkylene, arylene, or alkylene-arylene group, with 1 to 10 carbon atoms in each case, which can be interrupted by one or more oxygen or sulfur atoms or carboxyl or amino groups or can carry such atoms/groups at their end opposite the silicon atom, $R^1$ is a Z'-substituted, open-chain and/or cyclic alkylene, arylene, or alkylene-arylene group, with 1 to 10 carbon atoms in each case, which can be interrupted by one or more oxygen or sulfur atoms or carboxyl or amino groups or can carry such atoms/groups at their end opposite the silicon atom, R' is an open-chain and/or cyclic alkyl, alkenyl, aryl, or alkylaryl, or arylalkyl group, with preferably 1 to 20 carbon atoms, B and B' can be the same or different, both radicals can be a straight-chain or branched organically polymerizable group with at least one C=C double bond and at least 2 carbon atoms, instead of this B' can also mean $-R^2_aSiX_{4-a}$ or $-R^2_aR^1_bSiX_{4-a-b}$, where is an alkylene group with 1 to 10 carbon atoms and R' is defined as above, X is a group which can enter into a hydrolytic condensation reaction with the formation of Si—O—Si bridges, Z' is —CO(O)—, where the carbon atom is bound to the residue B',
a is 1 or 2,
and b is 0 or 1
comprising the following steps:
(a) preparation of a compound with the structure (II) or an isomer
a re-esterification product, or one of this compound's condensation products arising by loss of an alcohol molecule

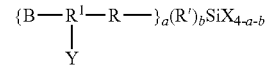  (II)

in which B, $R^1$, R, R', X, a, and b have the meanings specified in claim 1 for the structure (Ia) and Y is OH,
(b) reaction of this compound or of the isomer, re-esterification product,
or condensation product with a compound
B'C(O)X',
in which B' has the meaning specified in claim 1 for structure (Ia) and C(O)X' is a carboxylic acid group or an activated carbonyl compound, in particular an acid chloride or an acid anhydride,
and
(c) in given cases, workup of the product.

18. Silane according to claim 1, in which Z' is —NH—C(O)O— or —NH—C(O).

19. Silane according to claim 9, in which b is zero.

20. Silane according to claim 9, in which b is 1 and R' is a $C_1$-$C_4$ alkyl group.

21. Silane according to claim 18, in which b is 1 and R' is a $C_1$-$C_4$ alkyl group.

22. Silane according to claim 2, in which $R^1$ is a group with 1 to 4 carbon atoms.

\* \* \* \* \*

UNITED STATES PATENT AND TRADEMARK OFFICE
CERTIFICATE OF CORRECTION

| | | |
|---|---|---|
| PATENT NO. | : 7,932,414 B2 | |
| APPLICATION NO. | : 10/576514 | |
| DATED | : April 26, 2011 | |
| INVENTOR(S) | : Herbert Wolter | |

It is certified that error appears in the above-identified patent and that said Letters Patent is hereby corrected as shown below:

In column 2, line 34, change "$R^1$" to --$R'$--.

In column 5, line 35, change "-O-, -S-, -C(O)O-" to -- -O-, -S-, -NH-, or -C(O)- --.

In column 6, line 19, change "-$R^2_a$, $R^1_b SiX_{4-a-b}$," to -- -$R^2_a R^1_b SiX_{4-a-b}$,--.

In column 8, line 31, change "The reaction take" to --The reaction takes--.

In column 12, line 6, change "the silanes-proposed" to --the silanes proposed--.

In column 19, change " $\xrightarrow{A}$ " to -- $\xrightarrow{Cat.}$ --.

In column 19, the second reaction product from the fourth reaction is missing [OCH$_2$-CH$_2$]-CH$_2$-O-(CH$_2$)$_3$Si(OCH$_3$)$_3$. Correct column 19 to show the following:

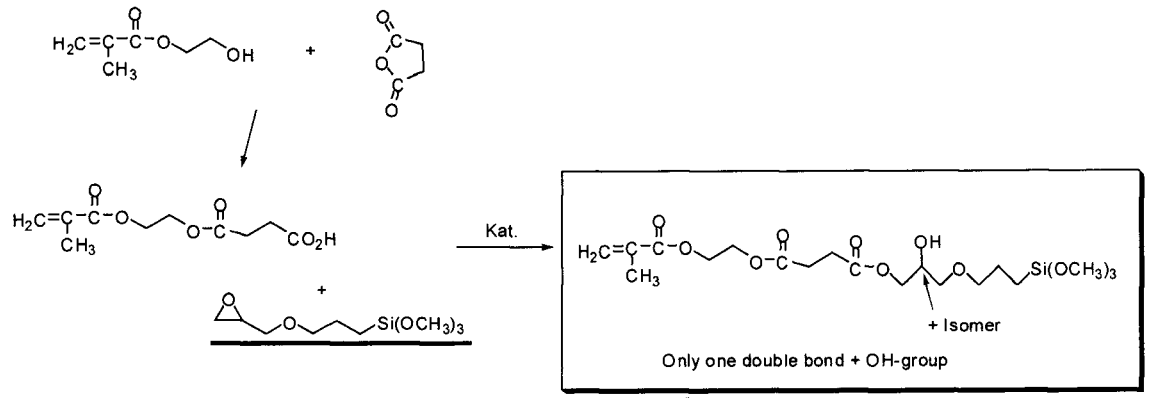

Signed and Sealed this
Fourteenth Day of August, 2012

David J. Kappos
*Director of the United States Patent and Trademark Office*

CERTIFICATE OF CORRECTION (continued)
U.S. Pat. No. 7,932,414 B2

In columns 21-22, beginning halfway down, the reactions should be as follows:

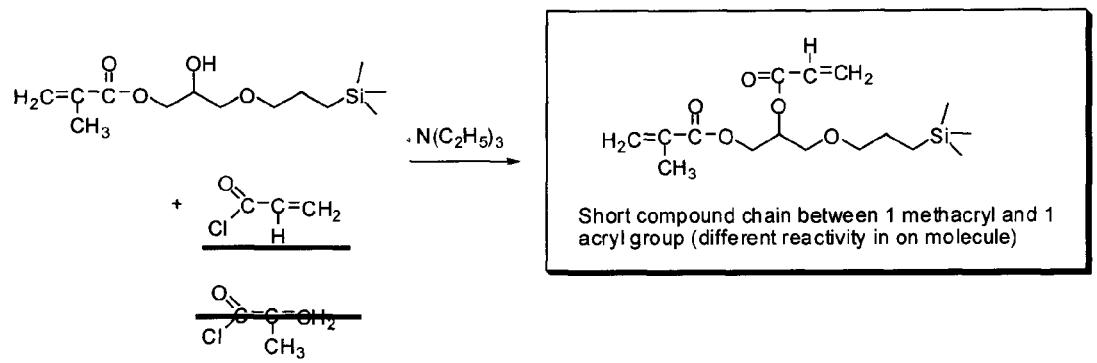

In columns 21-22, after the above reaction, the formulas should be as follows:

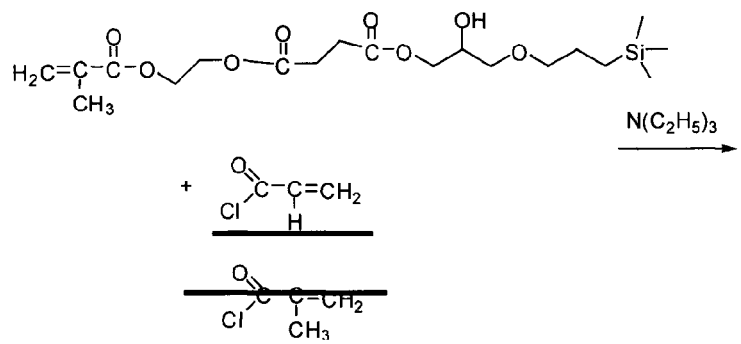

Starting at the bottom of columns 21-22 and continuing into columns 23-24, some of the sequences and reactions are missing. Change them to the following:

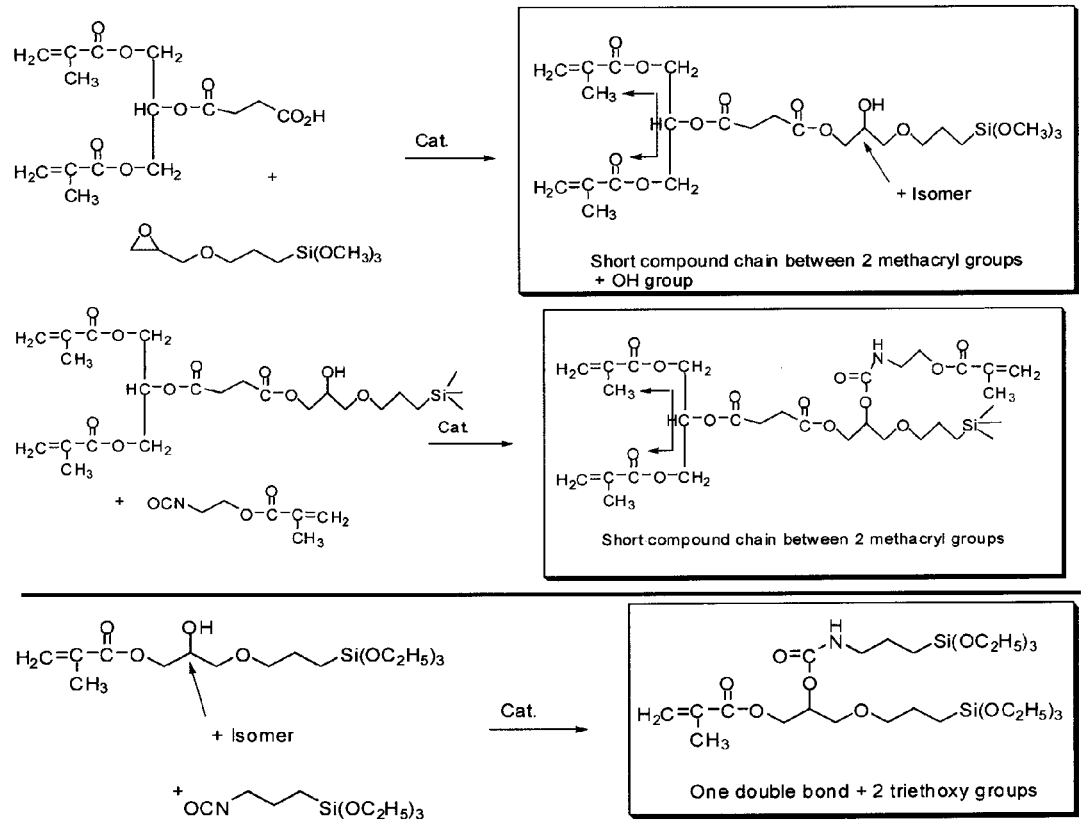

In column 25, line 30, change "carbon atom" to --carbon atoms--, and in line 62, "which carries B', a example, as" to --which carries B', a general increase in the strength of the cross-linked products can be achieved. Thus, the condensates according to the invention are suitable, for example, as,--.

In column 26, lines 61-63, change "$\square_{as(C=O)}$ = 1786 cm$^{-1}$, $\square_{sy(C=O)}$= 1864 cm$^{-1}$" to --$v_{as(C=O)}$ = 1786 cm$^{-1}$, $v_{sy(C=O)}$= 1864 cm$^{-1}$--.

In column 27, line 66, change "$\square$99% or $\square$88%" to --$\geq$99% or $\geq$88%--.

In column 28, line 58, change "125.0 g (0.503 mol) of 3-glycidyloxypropylmethyidi-" to --125.0 g (0.503 mol) of 3-glycidyloxypropylmethyldi- --.

In column 28, lines 66-67, change "$\square$99% or $\square$89%" to --$\geq$99% or $\geq$89%--.

In columns 29-30, change the formula scheme in example 4 to the following:

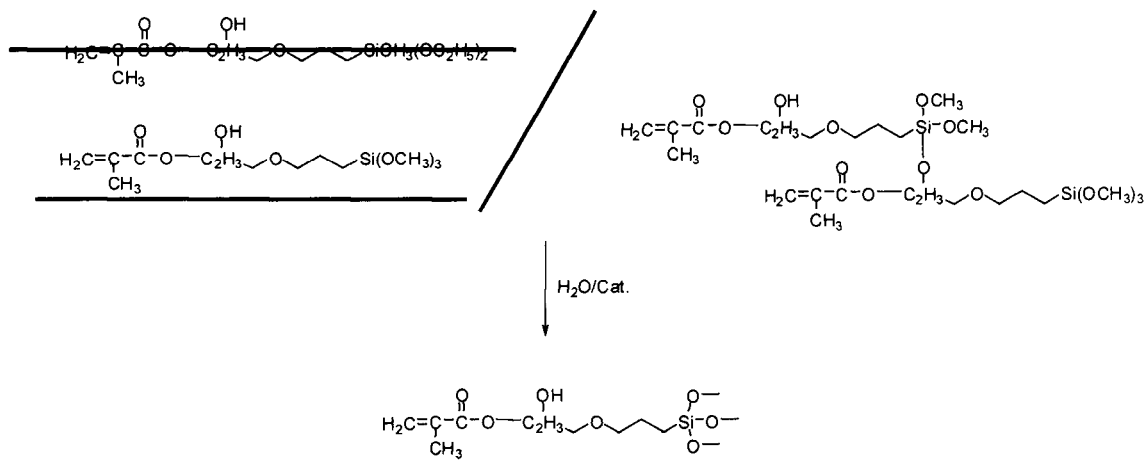

In column 31, before Example 8, change lines 31-37 to the following:

--IR data: $\nu_{(OH \leftarrow educt)} \sim 3500$ cm$^{-1}$, (unreacted OH since reaction was only with 0.7 moles of methacrylic acid isocyanatoethylester)

$\nu_{(NH \leftarrow urethane)} \sim 3370$ cm$^{-1}$ $\nu_{(C=O \leftarrow methacrylate/urethane)} \sim 1721$ cm$^{-1}$ $\nu_{(C=C \leftarrow methacrylate)} \sim 1638$ cm$^{-1}$ --.

In column 32, before Example 9, change lines 7-12 to the following:

--IR data: $\nu_{(OH \leftarrow educt)} \sim 3500$ cm$^{-1}$, (unreacted OH since reaction was only with 0.7 moles of methacrylic acid isocyanatoethylester)

$\nu_{(NH \leftarrow urethane)} \sim 3373$ cm$^{-1}$ $\nu_{(C=O \leftarrow methacrylate/urethane)} \sim 1721$ cm$^{-1}$ $\nu_{(C=C \leftarrow methacrylate)} \sim 1638$ cm$^{-1}$ --.

In column 33, line 16, please change "By means of the buoyancy method □ 2.1% by volume/" to --By means of the buoyancy method → 2.1% by volume/--.

In column 34, replace the Example 12 formula scheme with the following: